(12) United States Patent
Kelly et al.

(10) Patent No.: US 11,960,266 B1
(45) Date of Patent: Apr. 16, 2024

(54) PATIENT-SPECIFIC MEDICAL DEVICES AND ADDITIVE MANUFACTURING PROCESSES FOR PRODUCING THE SAME

(71) Applicant: RESTOR3D, INC., Durham, NC (US)

(72) Inventors: Cambre Kelly, Durham, NC (US); Hannah White, Durham, NC (US)

(73) Assignee: RESTOR3D, INC., Durham, NC (US)

( * ) Notice: Subject to any disclaimer, the term of this patent is extended or adjusted under 35 U.S.C. 154(b) by 0 days.

(21) Appl. No.: 18/454,580

(22) Filed: Aug. 23, 2023

(51) Int. Cl.
*B33Y 80/00* (2015.01)
*A61F 2/30* (2006.01)
(Continued)

(52) U.S. Cl.
CPC ...... *G05B 19/4099* (2013.01); *A61F 2/30942* (2013.01); *B33Y 50/00* (2014.12); *B33Y 80/00* (2014.12); *G06T 7/55* (2017.01); *G16H 30/20* (2018.01); *A61F 2002/30011* (2013.01); *A61F 2002/3092* (2013.01); *A61F 2002/3093* (2013.01); *A61F 2002/30952* (2013.01); *A61F 2002/30985* (2013.01); *A61F 2310/00011* (2013.01); *G05B 2219/35134* (2013.01); *G06T 2207/20081* (2013.01); *G06T 2207/30004* (2013.01)

(58) Field of Classification Search
CPC ...... G05B 19/4099; G05B 2219/35134; A61F 2/30942; A61F 2002/30011; A61F 2002/3092; A61F 2002/3093; A61F 2002/30952; A61F 2002/30985; A61F 2310/00011; B33Y 50/00; B33Y 80/00; G06T 7/55; G06T 2207/20081; G06T 2207/30004; G16H 30/20
See application file for complete search history.

(56) References Cited

U.S. PATENT DOCUMENTS

| 3,872,519 A | 3/1975 | Giannestras |
| 4,440,835 A | 4/1984 | Mgnaud |

(Continued)

FOREIGN PATENT DOCUMENTS

| CN | 109567913 A | 4/2019 |
| CN | 110090096 | 8/2019 |

(Continued)

OTHER PUBLICATIONS

Flaxman et al., A review and guide to creating patient specific 3D printed anatomical models from MRI for benign gynecologic surgery, 2021, 3D Printing in Medicine, pp. 1-10. (Year: 2021).*

(Continued)

*Primary Examiner* — Kidest Bahta
(74) *Attorney, Agent, or Firm* — Husch Blackwell LLP; Bryan D. Stewart; Sydney Forsander

(57) ABSTRACT

Systems and processes for designing and generating personalized surgical implants and devices are described herein. In various embodiments, the process includes generating patient-specific implants with patient-specific surface(s) and/or textures designed for increased osseointegration and improved surgical outcomes. In various embodiments, the process includes extracting patient-specific data with one or more aspects of an anatomical feature, processing the one or more aspects of the anatomical feature to create a non-rigid shape reference, and generating a patient-specific implant or device.

7 Claims, 13 Drawing Sheets

(51) Int. Cl.
  *B33Y 50/00* (2015.01)
  *G05B 19/4099* (2006.01)
  *G06T 7/55* (2017.01)
  *G16H 30/20* (2018.01)

(56) References Cited

U.S. PATENT DOCUMENTS

| | | |
|---|---|---|
| 4,588,574 A | 5/1986 | Felder et al. |
| 4,829,152 A | 5/1989 | Rostoker |
| 5,248,456 A | 9/1993 | Evans, Jr. et al. |
| 6,183,519 B1 | 2/2001 | Bonnin |
| 6,419,491 B1 | 7/2002 | Ricci |
| 6,461,358 B1 | 10/2002 | Faccioli |
| 7,001,672 B2 | 2/2006 | Justin et al. |
| 7,468,075 B2 | 12/2008 | Lang et al. |
| 7,534,246 B2 | 5/2009 | Reiley |
| 7,534,263 B2 | 5/2009 | Burdulis, Jr. et al. |
| 7,534,270 B2 | 5/2009 | Ball |
| D595,853 S | 7/2009 | Hanson |
| 7,618,451 B2 | 11/2009 | Berez et al. |
| 7,632,575 B2 | 12/2009 | Justin et al. |
| 7,634,119 B2 | 12/2009 | Tsougarakis et al. |
| 7,666,522 B2 | 2/2010 | Justin et al. |
| 7,717,956 B2 | 5/2010 | Lang |
| D623,749 S | 9/2010 | Horton |
| 7,796,791 B2 | 9/2010 | Tsougarakis et al. |
| 7,799,077 B2 | 9/2010 | Lang et al. |
| 7,981,158 B2 | 7/2011 | Fitz et al. |
| 8,062,302 B2 | 11/2011 | Lang et al. |
| 8,066,708 B2 | 11/2011 | Lang et al. |
| 8,077,950 B2 | 12/2011 | Tsougarakis et al. |
| 8,083,745 B2 | 12/2011 | Lang et al. |
| 8,094,900 B2 | 1/2012 | Steines et al. |
| 8,105,330 B2 | 1/2012 | Fitz et al. |
| 8,234,097 B2 | 1/2012 | Steines et al. |
| D653,756 S | 2/2012 | Courtney et al. |
| 8,122,582 B2 | 2/2012 | Burdulis, Jr. et al. |
| 8,142,886 B2 | 3/2012 | Noble et al. |
| 8,337,501 B2 | 12/2012 | Fitz et al. |
| 8,337,507 B2 | 12/2012 | Lang et al. |
| D675,320 S | 1/2013 | Oi |
| 8,343,218 B2 | 1/2013 | Lang et al. |
| 8,366,771 B2 | 2/2013 | Burdulis, Jr. et al. |
| 8,377,129 B2 | 2/2013 | Fitz et al. |
| 8,382,755 B2 | 2/2013 | Austin |
| 8,430,930 B2 | 4/2013 | Hunt |
| 8,439,926 B2 | 5/2013 | Bojarski et al. |
| 8,457,930 B2 | 6/2013 | Schroeder |
| 8,460,304 B2 | 6/2013 | Fitz et al. |
| 8,480,754 B2 | 7/2013 | Bojarski et al. |
| 8,485,820 B1 | 7/2013 | Ali |
| 8,500,740 B2 | 8/2013 | Bojarski et al. |
| 8,529,568 B2 | 9/2013 | Bouadi |
| 8,529,630 B2 | 9/2013 | Bojarski et al. |
| D692,136 S | 10/2013 | Tyber |
| 8,545,569 B2 | 10/2013 | Fitz et al. |
| 8,551,099 B2 | 10/2013 | Lang et al. |
| 8,551,102 B2 | 10/2013 | Fitz et al. |
| 8,551,103 B2 | 10/2013 | Fitz et al. |
| 8,551,169 B2 | 10/2013 | Fitz et al. |
| 8,551,173 B2 | 10/2013 | Lechmann et al. |
| 8,556,906 B2 | 10/2013 | Fitz et al. |
| 8,556,907 B2 | 10/2013 | Fitz et al. |
| 8,556,971 B2 | 10/2013 | Lang |
| 8,556,983 B2 | 10/2013 | Bojarski et al. |
| 8,561,278 B2 | 10/2013 | Fitz et al. |
| 8,562,611 B2 | 10/2013 | Fitz et al. |
| 8,562,618 B2 | 10/2013 | Fitz et al. |
| 8,568,479 B2 | 10/2013 | Fitz et al. |
| 8,568,480 B2 | 10/2013 | Fitz et al. |
| 8,585,708 B2 | 11/2013 | Fitz et al. |
| 8,617,172 B2 | 12/2013 | Fitz et al. |
| 8,617,242 B2 | 12/2013 | Philipp et al. |
| 8,623,026 B2 | 1/2014 | Wong et al. |
| 8,634,617 B2 | 1/2014 | Tsougarakis et al. |
| 8,638,998 B2 | 1/2014 | Steines et al. |
| 8,641,716 B2 | 2/2014 | Fitz et al. |
| 8,657,827 B2 | 2/2014 | Fitz et al. |
| 8,682,052 B2 | 3/2014 | Fitz et al. |
| 8,690,945 B2 | 4/2014 | Fitz et al. |
| 8,709,089 B2 | 4/2014 | Lang et al. |
| 8,715,362 B2 | 5/2014 | Reiley |
| 8,735,773 B2 | 5/2014 | Lang |
| D708,747 S | 7/2014 | Curran et al. |
| 8,768,028 B2 | 7/2014 | Lang et al. |
| 8,771,365 B2 | 7/2014 | Bojarski et al. |
| 8,775,133 B2 | 7/2014 | Schroeder |
| 8,828,311 B2 | 9/2014 | Medina et al. |
| 8,843,229 B2 | 9/2014 | Vanasse et al. |
| 8,882,847 B2 | 11/2014 | Burdulis, Jr. et al. |
| 8,888,485 B2 | 11/2014 | Ali |
| 8,906,107 B2 | 12/2014 | Bojarski et al. |
| 8,926,706 B2 | 1/2015 | Bojarski et al. |
| 8,932,363 B2 | 1/2015 | Tsougarakis et al. |
| D722,693 S | 2/2015 | Kaufmann et al. |
| 8,945,230 B2 | 2/2015 | Lang et al. |
| 8,951,259 B2 | 2/2015 | Fitz et al. |
| 8,951,260 B2 | 2/2015 | Lang et al. |
| 8,965,088 B2 | 2/2015 | Tsougarakis et al. |
| 8,974,539 B2 | 3/2015 | Bojarski et al. |
| 8,998,915 B2 | 4/2015 | Fitz et al. |
| 9,020,788 B2 | 4/2015 | Lang et al. |
| 9,023,050 B2 | 5/2015 | Lang et al. |
| 9,034,237 B2 | 5/2015 | Sperry et al. |
| 9,055,953 B2 | 6/2015 | Lang et al. |
| 9,066,728 B2 | 6/2015 | Burdulis, Jr. et al. |
| 9,072,531 B2 | 7/2015 | Fitz et al. |
| 9,084,617 B2 | 7/2015 | Lang et al. |
| D735,860 S | 8/2015 | Palinchik |
| D736,384 S | 8/2015 | Palinchik |
| 9,095,353 B2 | 8/2015 | Burdulis, Jr. et al. |
| 9,107,679 B2 | 8/2015 | Lang et al. |
| 9,107,680 B2 | 8/2015 | Fitz et al. |
| 9,113,921 B2 | 8/2015 | Lang et al. |
| 9,125,672 B2 | 9/2015 | Fitz et al. |
| 9,125,673 B2 | 9/2015 | Fitz et al. |
| 9,144,500 B2 | 9/2015 | Harding |
| 9,180,015 B2 | 11/2015 | Fitz et al. |
| 9,180,029 B2 | 11/2015 | Hollister et al. |
| 9,186,161 B2 | 11/2015 | Lang et al. |
| 9,186,254 B2 | 11/2015 | Fitz et al. |
| 9,186,257 B2 | 11/2015 | Geisler et al. |
| D745,159 S | 12/2015 | Lin |
| 9,216,025 B2 | 12/2015 | Fitz et al. |
| 9,220,516 B2 | 12/2015 | Lang et al. |
| 9,220,517 B2 | 12/2015 | Lang et al. |
| D747,485 S | 1/2016 | Oi |
| 9,241,724 B2 | 1/2016 | Lang et al. |
| 9,241,725 B2 | 1/2016 | Lang et al. |
| 9,271,845 B2 | 3/2016 | Hunt et al. |
| 9,295,482 B2 | 3/2016 | Fitz et al. |
| 9,295,562 B2 | 3/2016 | Lechmann et al. |
| 9,308,005 B2 | 4/2016 | Fitz et al. |
| 9,308,053 B2 | 4/2016 | Bojarski et al. |
| 9,308,060 B2 | 4/2016 | Ali |
| 9,308,091 B2 | 4/2016 | Lang |
| 9,314,256 B2 | 4/2016 | Fitz et al. |
| 9,320,620 B2 | 4/2016 | Bojarski et al. |
| 9,295,481 B2 | 5/2016 | Fitz et al. |
| 9,326,780 B2 | 5/2016 | Wong et al. |
| 9,333,058 B1 | 5/2016 | Krastev |
| 9,339,279 B2 | 5/2016 | Dubois et al. |
| 9,358,018 B2 | 6/2016 | Fitz et al. |
| 9,364,896 B2 | 6/2016 | Christensen et al. |
| 9,370,426 B2 | 6/2016 | Gabbrielli et al. |
| 9,375,222 B2 | 6/2016 | Fitz et al. |
| 9,387,079 B2 | 6/2016 | Bojarski et al. |
| 9,381,025 B2 | 7/2016 | Fitz et al. |
| 9,402,726 B2 | 8/2016 | Linderman et al. |
| 9,408,615 B2 | 8/2016 | Fitz et al. |
| 9,408,686 B1 | 8/2016 | Miller et al. |
| 9,415,137 B2 | 8/2016 | Meridew |
| 9,421,108 B2 | 8/2016 | Hunt |
| D767,137 S | 9/2016 | Lin |

(56) References Cited

U.S. PATENT DOCUMENTS

| | | |
|---|---|---|
| 9,433,510 B2 | 9/2016 | Lechmann et al. |
| 9,433,707 B2 | 9/2016 | Swords et al. |
| 9,439,767 B2 | 9/2016 | Bojarski et al. |
| 9,486,226 B2 | 11/2016 | Chao |
| 9,495,483 B2 | 11/2016 | Steines et al. |
| 9,517,134 B2 | 12/2016 | Lang |
| 9,545,317 B2 | 1/2017 | Hunt |
| 9,549,823 B2 | 1/2017 | Hunt et al. |
| 9,561,115 B2 | 2/2017 | Elahinia et al. |
| 9,572,669 B2 | 2/2017 | Hunt et al. |
| 9,579,110 B2 | 2/2017 | Bojarski et al. |
| 9,597,197 B2 | 3/2017 | Lechmann et al. |
| 9,603,711 B2 | 3/2017 | Bojarski et al. |
| 9,610,168 B2 | 4/2017 | Terrill |
| 9,636,226 B2 | 5/2017 | Hunt |
| 9,636,229 B2 | 5/2017 | Lang et al. |
| 9,649,178 B2 | 5/2017 | Ali |
| 9,662,157 B2 | 5/2017 | Schneider et al. |
| 9,662,226 B2 | 5/2017 | Wickham |
| 9,668,863 B2 | 6/2017 | Sharp et al. |
| 9,675,465 B2 | 6/2017 | Padovani et al. |
| 9,675,471 B2 | 6/2017 | Bojarski et al. |
| 9,681,956 B2 | 6/2017 | Al Hares et al. |
| 9,687,945 B2 | 6/2017 | Steines et al. |
| 9,688,026 B2 | 6/2017 | Ho et al. |
| 9,694,541 B2 | 7/2017 | Pruett et al. |
| 9,700,420 B2 | 7/2017 | Fitz et al. |
| 9,700,971 B2 | 7/2017 | Lang |
| 9,715,563 B1 | 7/2017 | Schroeder |
| 9,737,367 B2 | 8/2017 | Steines et al. |
| 9,750,613 B2 | 9/2017 | Petteys |
| 9,757,235 B2 | 9/2017 | Hunt et al. |
| 9,757,245 B2 | 9/2017 | O'Neil et al. |
| 9,775,680 B2 | 10/2017 | Bojarski et al. |
| 9,782,270 B2 | 10/2017 | Wickham |
| 9,788,972 B2 | 10/2017 | Flickinger et al. |
| 9,849,019 B2 | 12/2017 | Miller et al. |
| 9,872,773 B2 | 1/2018 | Lang et al. |
| 9,877,790 B2 | 1/2018 | Bojarski et al. |
| D809,661 S | 2/2018 | Mueller et al. |
| 9,907,670 B2 | 3/2018 | Deridder et al. |
| 9,910,935 B2 | 3/2018 | Golway et al. |
| 9,913,723 B2 | 3/2018 | Fitz et al. |
| 9,918,849 B2 | 3/2018 | Morris et al. |
| 9,925,054 B2 | 3/2018 | Siegler |
| 9,943,370 B2 | 4/2018 | Asseln et al. |
| 9,943,627 B2 | 4/2018 | Zhou et al. |
| 9,949,839 B2 | 4/2018 | Sander |
| 9,956,047 B2 | 5/2018 | Bojarski et al. |
| 9,956,048 B2 | 5/2018 | Bojarski et al. |
| D829,909 S | 10/2018 | Horton |
| 10,085,839 B2 | 10/2018 | Wong et al. |
| D835,278 S | 12/2018 | Gottlieb |
| 10,183,442 B1 | 1/2019 | Miller |
| 10,245,152 B2 | 4/2019 | Kloss |
| D849,944 S | 5/2019 | Dacosta |
| 10,278,823 B1 | 5/2019 | Xue |
| D850,620 S | 6/2019 | Tyber |
| D855,184 S | 7/2019 | Predick |
| 10,357,377 B2 | 7/2019 | Nyahay |
| D858,769 S | 9/2019 | Barela et al. |
| 10,449,051 B2 | 10/2019 | Hamzey |
| 10,492,686 B2 | 12/2019 | Hunter |
| D877,907 S | 3/2020 | Linder et al. |
| D878,589 S | 3/2020 | Linder |
| D878,590 S | 3/2020 | Linder et al. |
| D879,295 S | 3/2020 | Abbasi |
| D879,961 S | 3/2020 | Linder et al. |
| D881,665 S | 4/2020 | Zemel et al. |
| 10,624,746 B2 | 4/2020 | Jones et al. |
| 10,667,924 B2 | 6/2020 | Nyahay |
| 10,744,001 B2 | 8/2020 | Sack |
| 10,772,732 B1 | 9/2020 | Miller et al. |
| D899,900 S | 10/2020 | Blanco |
| 10,940,015 B2 | 3/2021 | Sack |
| D920,515 S | 5/2021 | Miller |
| D920,516 S | 5/2021 | Miller |
| D920,517 S | 5/2021 | Miller |
| 11,026,798 B1 | 6/2021 | Miller |
| 11,033,394 B2 | 6/2021 | Hamzey |
| 11,135,771 B1 | 10/2021 | Reith |
| D938,033 S | 12/2021 | Dang |
| 11,324,525 B1 | 5/2022 | Garvey |
| 11,353,277 B2 | 6/2022 | Muceus |
| 11,439,726 B2 | 9/2022 | Spence |
| 11,471,203 B2 | 10/2022 | Sutika |
| 11,666,452 B2 | 6/2023 | Melkent et al. |
| 11,744,716 B2 | 9/2023 | Jebsen et al. |
| 2004/0148032 A1 | 7/2004 | Rutter et al. |
| 2006/0249875 A1 | 11/2006 | Robb et al. |
| 2007/0100346 A1 | 5/2007 | Wyss |
| 2007/0118243 A1 | 5/2007 | Schroeder et al. |
| 2008/0206297 A1 | 8/2008 | Roeder et al. |
| 2009/0093668 A1 | 4/2009 | Marten et al. |
| 2009/0182430 A1 | 7/2009 | Tyber et al. |
| 2010/0137990 A1 | 6/2010 | Apatsidis et al. |
| 2010/0168798 A1 | 7/2010 | Clineff et al. |
| 2010/0286791 A1 | 11/2010 | Goldsmith |
| 2011/0144752 A1 | 6/2011 | Defelice et al. |
| 2011/0190898 A1 | 8/2011 | Lenz |
| 2011/0224796 A1 | 9/2011 | Weiland et al. |
| 2011/0230974 A1 | 9/2011 | Musani |
| 2012/0064288 A1 | 3/2012 | Nakano et al. |
| 2012/0215310 A1 | 8/2012 | Sharp et al. |
| 2013/0068968 A1 | 3/2013 | Daniel |
| 2013/0123935 A1 | 5/2013 | Hunt et al. |
| 2013/0158651 A1 | 6/2013 | Hollister et al. |
| 2013/0197657 A1 | 8/2013 | Anca et al. |
| 2013/0218282 A1 | 8/2013 | Hunt |
| 2013/0274890 A1 | 10/2013 | McKay |
| 2013/0296874 A1 | 11/2013 | Chao |
| 2014/0100779 A1 | 4/2014 | Tuke |
| 2014/0107785 A1 | 4/2014 | Geisler et al. |
| 2014/0107786 A1 | 4/2014 | Geisler et al. |
| 2014/0236299 A1 | 8/2014 | Roeder et al. |
| 2014/0277443 A1 | 9/2014 | Fleury et al. |
| 2014/0277452 A1 | 9/2014 | Skaer |
| 2014/0288650 A1 | 9/2014 | Hunt |
| 2014/0336680 A1 | 11/2014 | Medina et al. |
| 2014/0350688 A1 | 11/2014 | Michel |
| 2014/0371863 A1 | 12/2014 | Vanasse et al. |
| 2015/0025666 A1* | 1/2015 | Olivieri .................. G06F 30/00 700/98 |
| 2015/0105858 A1 | 4/2015 | Papay et al. |
| 2015/0282945 A1 | 10/2015 | Hunt |
| 2015/0282946 A1 | 10/2015 | Hunt |
| 2015/0320461 A1 | 11/2015 | Ehmke |
| 2015/0335434 A1 | 11/2015 | Patterson et al. |
| 2015/0343709 A1 | 12/2015 | Gerstle et al. |
| 2015/0351915 A1 | 12/2015 | Defelice et al. |
| 2016/0008139 A1 | 1/2016 | Siegler |
| 2016/0051371 A1 | 2/2016 | Defelice et al. |
| 2016/0089138 A1 | 3/2016 | Early et al. |
| 2016/0151833 A1 | 6/2016 | Tsao |
| 2016/0193055 A1 | 7/2016 | Ries |
| 2016/0199193 A1 | 7/2016 | Willis et al. |
| 2016/0213485 A1 | 7/2016 | Schaufler et al. |
| 2016/0213486 A1 | 7/2016 | Nunley et al. |
| 2016/0213487 A1 | 7/2016 | Wilson et al. |
| 2016/0213488 A1 | 7/2016 | Moore et al. |
| 2016/0220288 A1 | 8/2016 | Dubois et al. |
| 2016/0256279 A1 | 9/2016 | Sanders et al. |
| 2016/0256610 A1 | 9/2016 | Zhou et al. |
| 2016/0270931 A1 | 9/2016 | Trieu |
| 2016/0287388 A1 | 10/2016 | Hunt et al. |
| 2016/0303793 A1 | 10/2016 | Ermoshkin et al. |
| 2016/0333152 A1 | 11/2016 | Cook et al. |
| 2016/0374829 A1 | 12/2016 | Vogt et al. |
| 2017/0014169 A1 | 1/2017 | Dean et al. |
| 2017/0020685 A1 | 1/2017 | Geisler et al. |
| 2017/0036403 A1 | 2/2017 | Ruff et al. |
| 2017/0042697 A1 | 2/2017 | McShane, III et al. |
| 2017/0056178 A1 | 3/2017 | Sharp et al. |
| 2017/0056179 A1 | 3/2017 | Lorio |

(56) References Cited

U.S. PATENT DOCUMENTS

| | | |
|---|---|---|
| 2017/0066873 A1 | 3/2017 | Gardet |
| 2017/0105844 A1 | 4/2017 | Kuyler et al. |
| 2017/0156880 A1 | 6/2017 | Halverson et al. |
| 2017/0165085 A1 | 6/2017 | Lechmann et al. |
| 2017/0165790 A1 | 6/2017 | McCarthy et al. |
| 2017/0172758 A1 | 6/2017 | Field et al. |
| 2017/0182222 A1 | 6/2017 | Paddock et al. |
| 2017/0018919 A1 | 7/2017 | Reiley |
| 2017/0209274 A1 | 7/2017 | Beerens et al. |
| 2017/0216035 A1 | 8/2017 | Hunt |
| 2017/0216036 A1 | 8/2017 | Cordaro |
| 2017/0239054 A1 | 8/2017 | Engstrand et al. |
| 2017/0239064 A1 | 8/2017 | Cordaro |
| 2017/0245998 A1 | 8/2017 | Padovani et al. |
| 2017/0252165 A1 | 9/2017 | Sharp et al. |
| 2017/0258606 A1 | 9/2017 | Afzal |
| 2017/0282455 A1 | 10/2017 | Defelice et al. |
| 2017/0296244 A1 | 10/2017 | Schneider et al. |
| 2017/0319344 A1 | 11/2017 | Hunt |
| 2017/0323037 A1 | 11/2017 | Schroeder |
| 2017/0333205 A1 | 11/2017 | Joly et al. |
| 2017/0354510 A1 | 12/2017 | O'Neil et al. |
| 2017/0354513 A1 | 12/2017 | Maglaras et al. |
| 2017/0355815 A1 | 12/2017 | Becker et al. |
| 2017/0360488 A1 | 12/2017 | Kowalczyk et al. |
| 2017/0360563 A1 | 12/2017 | Hunt et al. |
| 2017/0360578 A1 | 12/2017 | Shin et al. |
| 2017/0367843 A1 | 12/2017 | Eisen et al. |
| 2017/0367844 A1 | 12/2017 | Eisen et al. |
| 2017/0367845 A1 | 12/2017 | Eisen et al. |
| 2018/0008419 A1 | 1/2018 | Tyber et al. |
| 2018/0012517 A1* | 1/2018 | Ropelato ................ G09B 23/32 |
| 2018/0022017 A1 | 1/2018 | Fukumoto et al. |
| 2018/0064540 A1 | 3/2018 | Hunt |
| 2018/0098858 A1 | 4/2018 | Valderraband |
| 2018/0104063 A1 | 4/2018 | Asaad |
| 2018/0110593 A1 | 4/2018 | Khalil |
| 2018/0110626 A1 | 4/2018 | McShane, III et al. |
| 2018/0110627 A1 | 4/2018 | Sack |
| 2018/0117219 A1 | 5/2018 | Yang et al. |
| 2018/0147319 A1 | 5/2018 | Colucci-Mizenko et al. |
| 2018/0256336 A1 | 9/2018 | Mueller et al. |
| 2018/0280140 A1 | 10/2018 | Jones |
| 2018/0289380 A1 | 10/2018 | Mauldin |
| 2018/0289515 A1 | 10/2018 | Nemes et al. |
| 2019/0167433 A1 | 6/2019 | Allen |
| 2019/0262101 A1 | 8/2019 | Shanjani et al. |
| 2019/0302736 A1* | 10/2019 | Chanin ................ B33Y 50/00 |
| 2019/0343652 A1 | 11/2019 | Petersheim et al. |
| 2020/0000595 A1 | 1/2020 | Jones |
| 2020/0030102 A1 | 1/2020 | Mullens et al. |
| 2020/0046512 A1 | 2/2020 | Newman et al. |
| 2020/0085452 A1 | 3/2020 | Siegler |
| 2020/0085585 A1 | 3/2020 | Siegler |
| 2020/0155321 A1 | 5/2020 | Dikovsky |
| 2020/0171752 A1 | 6/2020 | Rogren |
| 2020/0171753 A1 | 6/2020 | Satko |
| 2020/0367910 A1 | 11/2020 | Hafez et al. |
| 2021/0077276 A1 | 3/2021 | Garvey et al. |
| 2021/0110605 A1* | 4/2021 | Haslam ................ G06V 10/26 |
| 2021/0216683 A1 | 7/2021 | Rai |
| 2021/0298908 A1 | 9/2021 | Holmes |
| 2021/0340334 A1 | 11/2021 | Portela |
| 2022/0023048 A1 | 1/2022 | Nolens |
| 2022/0087670 A1 | 3/2022 | Selmoune |
| 2022/0134639 A1 | 5/2022 | Allen |
| 2022/0142783 A1 | 5/2022 | Ahmadi |
| 2022/0168109 A1 | 6/2022 | Giordano |
| 2022/0296386 A1 | 9/2022 | Fang |

FOREIGN PATENT DOCUMENTS

| | | |
|---|---|---|
| DE | 69806985 | 6/2003 |
| EP | 1180989 | 4/2006 |
| EP | 2832321 | 2/2015 |
| EP | 2635239 | 7/2017 |
| EP | 2913030 | 3/2018 |
| EP | 3586800 | 1/2020 |
| FR | 3071400 | 3/2019 |
| JP | 4840886 | 12/2011 |
| KR | 301007894 | 5/2019 |
| WO | 2014020562 | 2/2014 |
| WO | 2015054070 A1 | 4/2015 |
| WO | 2020123295 A1 | 6/2020 |

OTHER PUBLICATIONS

Extended European Search Report dated Feb. 12, 2021 for European Patent Application No. EP20196410.3.

Larraona et al., "Radiopaque material for 3D printing scaffolds", XXXV Confreso Anual de la Sociedad Espanola de Ingenieria Biomedica. Bilbao, Nov. 29-Dec. 1, 2017, p. 451-454 (Year: 2017).

Rozema et al., The effects of different steam-sterilization programs on material properties of poly(I-lactide), Journal of Applied Biomaterials, vol. 2, 23-28 (1991) (Year: 1991).

Alt, Sami. "Design for Sterilization Part 1: Steam Sterillization." Material, Material Technology Blog, Jun. 3, 2016, www.material-technology.com/single-post/2016/05/24/Design-for-Sterilization-part-1-Steam-Sterillization.

Ducheyne, Paul. "Comprehensive Biomaterials." Comprehensive Biomaterials, vol. 1, Elsevier, 2011, pp. 135-135.

Anat Ratnovsky et al., Mechanical Properties of Different Airway Stents, Med. Eng'g. Physics, Mar. 2011, at 408., http://www.medengphys.com/article/S1350-4533(15)00042-9/fulltext.

Andrew T. Miller et al., Fatigue of Injection Molded and 3D Printed Polycarbonate Urethane in Solution, 108 Polymer 121 (2017).

Andrew T. Miller et al., Deformation and Fatigue of Tough 3D Printed Elastomer Scaffolds Processed by Fused 3 Deposition Modeling and Continuous Liquid Interface Production, 75 J. Mechanical Behavior Biomedical Materials 1 (2017).

Ortho Spine News, "SeaSpine Announces 25,000th NanoMetalene Implantation", first available Dec. 18, 2019. (https://orthospinenews.com/2019/12/18/seaspine-announces-25000th-nanometalene-implantation/) (Year: 2019).

Restor3d, "Products", first available Sep. 28, 2020. (https://web.archive.org/web/20200928123335/https:/restor3d.com/products) (Year: 2020).

Ortho Spine News, "Nvision Biomedical Technologies: First FDA Clearance for Osteotomy Wedge System", first available Oct. 28, 2020. (https://orthospinenews.com/2020/10/28/nvision-biomedical-technologies-first-fda-clearance-for-osteotomy-wedge-system-made-of-peek-optima-ha-enhanced/) (Year: 2020).

Sina, "Application logic of triple periodic minimum surface", first available Oct. 24, 2020. (https://k.sina.com.cnarticle_2422410454_90630cd6001 00tlbm.html?from=science) (Year: 2020).

3D Adept Media, "Johnson & Johnson Medical", first available Sep. 17, 2018. (https://3dadept.com/johnson-johnson-medical-has-acquired-3d-printed-spmplants-special ist-emerging-implant-technologies/) (Year: 2018).

Additive Orthopaedics, "Additive Orthopaedics 3d Printed Cotton Bone Segment", first available Sep. 19, 2020. (https://web.archive.org/web/20200919145251/https:/www.additiveorthopaedics.com/our-products/cotton/) (Year: 2020).

Indiamart, "Anterior Cervical Fusion Cage for Spine Surgery", first accessed Dec. 9, 2020. (https://www.indiamart.com/ proddetail/anterior-cervical-fusion-cage-12402896897 .html) (Year: 2020).

Instagram, "restor3d", first available Jul. 21, 2020. (https://www.instagram.com/p/CC6dztOAKcM/?utm_source=ig_web_link) (Year: 2020).

* cited by examiner

PATIENT-SPECIFIC MEDICAL DEVICES AND ADDITIVE MANUFACTURING PROCESSES FOR PRODUCING THE SAME

BACKGROUND

Conventional surgical implants come in a variety of discrete sizes, but generally lack patient-specific sizing or other customization. Some surgical implants include patient-specific surfaces, but such surfaces may be based on incomplete patient anatomy data. Generally speaking, existing surgical implant production and analysis systems lack the ability to efficiently and dynamically evaluate a compilation of an entire complex data model to design and build a personalized reference model. Thus, existing systems and processes may produce inferior surgical devices with inaccurate surface structures based on these less than ideal personalized reference models.

Therefore, there is an unmet and unsolved need for patient-specific devices with higher accuracy patient-specific surfaces (and other features) and systems and processes for producing such patient-specific devices.

BRIEF SUMMARY OF THE DISCLOSURE

Briefly described, and according to one embodiment, aspects of the present disclosure generally relate to patient-specific implants and systems and processes for producing the same. In at least one embodiment, a patient-specific device can include an implant, instrument, surgical guide, cut guide, tools, or any other patient, consumer, or animal-specific use-case. In various embodiments, the patient-specific device may be a 3D printed medical device. In some embodiments, the patient-specific device can include one or more surfaces, features, and other parameters that are customized and tailored for a patient's anatomy to improve mechanical performance and surgical outcomes. In at least this way, aspects of the present disclosure provide an implant device, a cut guide, or similar medical device, that is contoured to accurately align with the structures and surface textures of a patient's existing anatomy to provide better fit and function of the surgical implant or device. In some embodiments, the patient-specific device can include at least one porous area comprising a lattice structure configured to promote osseointegration. In some embodiments, the patient-specific device can include a cut guide with at least one textured area comprising a lattice structure configured to increase friction and improve surgical outcomes.

The patient-specific devices discussed herein may include at least one patient-specific, artificial intelligence derived surface. In at least one embodiment, patient-specific devices discussed herein include a patient-specific surface for mating with a portion of the patient's bone anatomy and a non-patient specific surface for articulation, mating with another portion of the patient's anatomy, etc. In one or more embodiments, the patient-specific device includes only patient-specific (e.g., custom to the patient) surfaces.

According to particular embodiments, a patient-specific device (e.g., implant, instrument, trial, surgical guide, etc.) may be designed and manufactured via one or more systems and processes that leverage advanced surgical planning, implant design, and additive manufacturing/3D-printing. In various embodiments, the disclosed processes and systems automatically or semi-automatically design patient-specific devices based on input/received data. Such as, for example, leveraging artificial intelligence techniques to design a patient anatomy model based on received 2D patient images and then using the patient anatomy model to generate, design, or produce one or more surfaces on a patient-specific device that corresponds to the anatomy of the patient anatomy model.

According to a first aspect, the present disclosure includes a medical device production process comprising: populating a database with: a plurality of 2D image packages, each of the plurality of 2D image packages comprising a series of 2D image files of patient-specific anatomy; a plurality of patient anatomical representations, each of the plurality of patient anatomical representations associated with at least one of the plurality of 2D image packages; a plurality of patient-specific device files, each of the plurality of patient-specific device files associated with at least one of the plurality of patient anatomical representations; receiving a 2D image package associated with a particular patient and including a series of 2D images files associated with an anatomical feature of the particular patient; extracting one or more aspects of the anatomical feature of the particular patient from the 2D image package; processing the one or more aspects of the anatomical feature via an artificial intelligence model to create a non-rigid shape reference based upon the plurality of patient anatomical representations and patient-specific device files; and generating a digital representation of at least one patient-specific device based on the non-rigid shape reference of the anatomical feature of the particular patient and the database.

In a second aspect of the process of the first aspect or any other aspect, wherein the patient-specific device comprises a patient-specific implant.

In a third aspect of the process of the first aspect or any other aspect, wherein the patient-specific device comprises a patient-specific instrument.

In a fourth aspect of the process of the first aspect or any other aspect, wherein the artificial intelligence model is a particular artificial intelligence model; and generating the digital representation of the at least one patient-specific device is based on: the 3D digital representation of the anatomical feature of the particular patient; the plurality of patient-specific device files; and processing the one or more aspects of the anatomical feature via a specific artificial intelligence model.

In a fifth aspect of the process of the fourth aspect or any other aspect, wherein the specific artificial intelligence model outputs a patient-specific device file based on a compilation of the plurality of patient-specific device files.

In a sixth aspect of the process of the fifth aspect or any other aspect, wherein generating the digital representation of the at least one patient-specific device comprises processing the one or more aspects of the anatomical feature, the 3D digital representation of the anatomical feature of the particular patient, and the plurality of patient-specific device files via the artificial intelligence.

In a seventh aspect of the process of the fourth aspect or any other aspect, wherein the specific artificial intelligence model is the particular artificial intelligence model.

According to an eighth aspect, a process for training an artificial intelligence model comprising: receiving a 2D image file package comprising patient anatomy data; extracting one or more aspects from the patient anatomy data; processing the one or more aspects of the patient anatomy data via an artificial intelligence model to generate a 3D digital representation of at least a portion of the patient anatomy data; comparing the 3D digital representation to a known 3D digital representation; updating one or more emphasis guidelines of the artificial intelligence model based on the comparing step; and upon a determination that at least a portion of the 3D digital representation and at least a portion of the known 3D digital representation are within a preconfigured threshold, saving the updated one or more emphasis guidelines.

In a ninth aspect of the process of the eighth aspect or any other aspect, further comprising: receiving a second 2D image file package comprising second patient anatomy data; extracting one or more second aspects from the second patient anatomy data; processing the one or more second aspects from the second patient anatomy data via the artificial intelligence model using the updated one or more emphasis guidelines, and generating a second 3D digital representation of at least a portion of the second patient anatomy data.

In a tenth aspect of the process of the ninth aspect or any other aspect, further comprising generating a CAD file for at least one patient-specific implant based on the 3D digital representation.

In an eleventh aspect of the process of the ninth aspect or any other aspect, further comprising generating a CAD file for at least one patient-specific instrument based on the 3D digital representation.

In a twelfth aspect of the process of the eighth aspect or any other aspect, further comprising: generating a CAD file for at least one patient-specific device; wherein the artificial intelligence model is a particular artificial intelligence model; and generating the CAD file for the at least one patient-specific device is based on: the 3D digital representation of the at least one aspects of the patient anatomy data; the 2D image file package; and processing the one or more aspects of the patient anatomy data via a specific artificial intelligence model.

In a thirteenth aspect of the process of the twelfth aspect or any other aspect, wherein the specific artificial intelligence model outputs a patient-specific device file based on a compilation of a plurality of patient-specific device files included in the 2D image file package. In a fourteenth aspect of the process of the twelfth aspect or any other aspect, wherein generating the CAD file for the at least one patient-specific device comprises processing the at least one aspect of the patient anatomy data, the 3D digital representation of at least a portion of the patient anatomy data, and the 2D image file package via the artificial intelligence model.

According to a fifteenth aspect, a process for training an artificial intelligence model comprising: receiving a DICOM file comprising patient anatomy data; extracting one or more aspects from the patient anatomy data; processing the one or more aspects of the patient anatomy data via an artificial intelligence model to generate a 3D device model for replacing a portion of the patient anatomy; comparing a portion of the 3D device model of a portion of a known 3D device model; updating one or more emphasis guidelines of the artificial intelligence model based on the comparing step, the one or more emphasis guidelines associated with one or more of a 3D digital representation of healthy anatomy, an device model, and previously stored patient anatomy; and upon a determination that the portion of the 3D device model and the portion of the known 3D device model is within a preconfigured threshold, saving the updated one or more emphasis guidelines.

In a sixteenth aspect of the process of the fifteenth aspect or any other aspect, further comprising: receiving a second DICOM file package comprising second patient anatomy data; extracting one or more second aspects from the second patient anatomy data; processing the one or more second aspects from the second patient anatomy data via the artificial intelligence model using the updated one or more emphasis guidelines; and generating a second 3D device model of at least a portion of the second patient anatomy data.

In a seventeenth aspect of the process of the fifteenth aspect or any other aspect, further comprising: generating a CAD file for at least one patient-specific device; wherein the artificial intelligence model is a particular artificial intelligence model; and generating the CAD file for the at least one patient-specific device is based on: the 3D digital representation of the at least one or more aspects of the patient anatomy data; the DICOM file; and processing the one or more aspects of the patient anatomy data via a specific artificial intelligence model.

In an eighteenth aspect of the process of the seventeenth aspect or any other aspect, wherein the patient-specific device comprises a patient-specific implant.

In a nineteenth aspect of the process of the seventeenth aspect or any other aspect, wherein the patient-specific device comprises a patient-specific instrument.

In a twentieth aspect of the process of the seventeenth aspect or any other aspect, wherein generating the CAD file for the at least one patient-specific device comprises processing the at least one or more aspects of the patient anatomy data, the 3D digital representation of at least a portion of the patient anatomy data, and the DICOM file via the artificial intelligence model.

According to a twenty-first aspect, a medical device comprising: a 3D-printed body, the 3D-printed body defining at least one opening for receiving a fixation device and comprising: a metallic material, a patient-specific surface derived from a non-rigid model representing patient anatomy, the non-rigid model produced at least in part by an artificial intelligence model based on one or more feature extracted from a 2D image package comprising images of the patient anatomy, and at least one porous area comprising a lattice structure and configured to promote osseointegration with the at least one porous area.

In a twenty-second aspect of the medical device of the twenty-first aspect or any other aspect, wherein the non-rigid model comprises one or more points excluded from the one or more features.

In a twenty-third aspect of the medical device of the twenty-second aspect or any other aspect, wherein the one or more points are excluded from the 2D image package.

In a twenty-fourth aspect of the medical device of the twenty-third aspect or any other aspect, wherein the one or more points are produced by the artificial intelligence model.

In a twenty-fifth aspect of the medical device of the twenty-fourth aspect or any other aspect, wherein the patient-specific surface includes a surface feature mirroring the one or more points.

In a twenty-sixth aspect of the medical device of the twenty-fifth aspect or any other aspect, wherein the at least one porous area comprises the patient-specific surface.

In a twenty-seventh aspect of the medical device of the twenty-sixth aspect or any other aspect, wherein the 3D-printed body comprises at least one non-porous area.

According to a twenty-eighth aspect, an orthopedic medical device comprising: a 3D-printed body, the 3D-printed body comprising: a metallic material; a patient-specific surface derived from a non-rigid model representing patient anatomy, the non-rigid model produced at least in part by an artificial intelligence model based on one or more features extracted from a 2D image package comprising images of the patient anatomy; and at least one porous area comprising a lattice structure and configured to promote tissue integration.

These and other aspects, features, and benefits of the systems and processes described herein will become apparent from the following detailed written description taken in conjunction with the following drawings, although variations and modifications thereto may be affected without departing from the spirit and scope of the novel concepts of the disclosure.

BRIEF DESCRIPTION OF THE DRAWINGS

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein.

Figure 1:
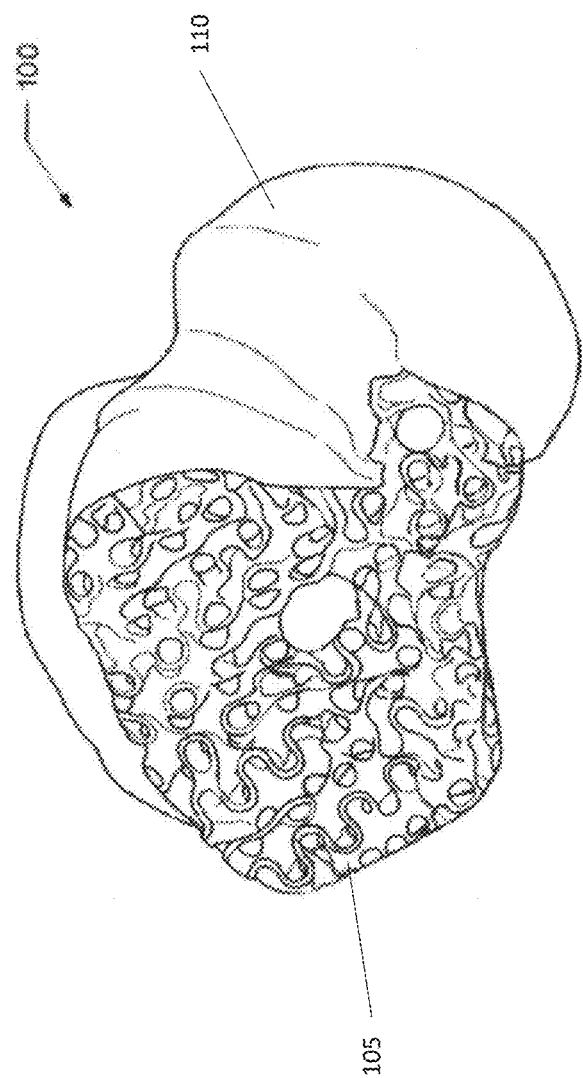
FIG. 1 illustrates an exemplary personalized surgical implant with patient-specific surfaces generated according to one embodiment of the present disclosure.

While the disclosure is susceptible to various modifications and alternative forms, specific embodiments thereof are shown by way of example in the drawings and will herein be described in detail. It should be understood, however, that the drawings and detailed description presented herein are not intended to limit the disclosure to the particular embodiment disclosed, but on the contrary, the intention is to cover all modifications, equivalents, and alternatives falling within the spirit and scope of the present disclosure.

DETAILED DESCRIPTION

To promote an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined by and as expressed in the claims.

Whether a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

Overview

In various embodiments, aspects of the present disclosure generally relate to systems and processes for creating and generating a personalized surgical implant using a plurality of patient files and associated data elements. The system may leverage a plurality of advanced data transformation processes to produce personalized surgical devices with one or more patient-specific surfaces using a dynamic and scalable analytics system to promote osseointegration and/or cut guide friction and improve surgical outcomes for a particular patient.

In some embodiments, the system is a platform for extracting and evaluating patient-specific anatomical features from a plurality of patient data files and associated data elements, and other parameters to create an advanced customized device generation process. For example, in at least one embodiment, the system leverages a patient-specific surface design to create a surgical implant device with a customized porous architecture designed for osseointegration, a fully interconnected lattice structure, and a maximized surface area to provide a patient-specific implant surface. In another non-limiting embodiment, the system leverages a patient-specific design to create a contoured surgical cut guide device with a customized shape and texture for increased friction to provide a patient-specific cut guide surface to improve surgical procedures for both the provider and the patient.

DESCRIPTION OF THE FIGURES

For the purposes of example and explanation of the fundamental processes and components of the disclosed systems and processes, reference is made to the figures. In general, the figures illustrate patient-specific devices produced by processes discussed herein and exemplary systems and processes for producing such devices.

Exemplary Patient-Specific Devices

FIG. 1 illustrates a non-limiting example of a side view of a patient-specific surgical implant 100 generated according to embodiments of the present disclosure. Various aspects of the embodiment shown in FIG. 1 include one or more patient-specific surfaces 105 and 110. In some embodiments, the patient-specific surfaces 105 and 110 can include one or more porous, smooth, or textured surface features, and/or other features, as described in connection with the implant data 1155 and computer aided design (CAD) model data 1160, described in connection with FIG. 11. For example, the implant 100 can include a first patient-specific surface 105 that may include a porous surface including one or more lattice structures. In some embodiments, the one or more lattice structures can include, but is not limited to, a surface lattice, a strut lattice, a planar-based lattice, a beam lattice, a TPMS lattice (e.g., gyroid), a honeycomb lattice, periodic lattice, a stochastic lattice (e.g., Voronoi), and similar. The implant 100 can include a second patient-specific surface 110 with a different shape, dimension, configuration, porosity, surface texture, etc. than the first patient-specific surface 105, in some embodiments.

As will be understood from discussions herein, exemplary implant 100 may be produced from patient images and information, which may be saved in memory. It will be appreciated that FIG. 1 is only a non-limiting embodiment and configurations, dimensions, and other parameters of a personalized surgical implant can be generated according to the system and processes described herein.

Figure 2:
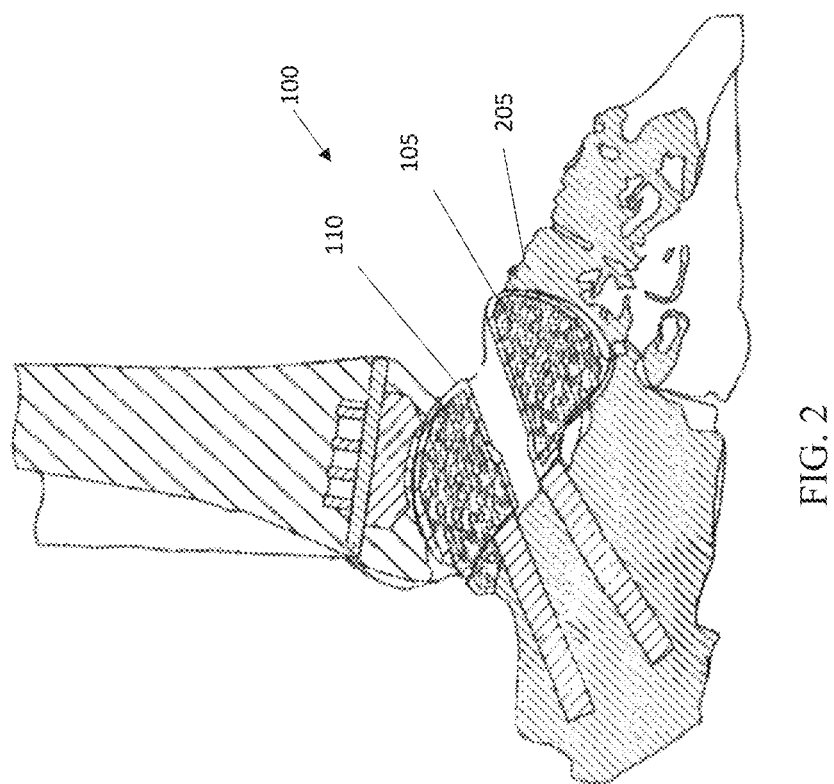
FIG. 2 illustrates an exemplary personalized surgical implant with patient-specific surfaces generated according to one embodiment of the present disclosure.

FIG. 2 illustrates a cross-sectional view of implant 100 in the context of patient anatomy, according to embodiments of the present disclosure. In some embodiments, the implant 100 may include one or more patient-specific surfaces 110 and 105. In some embodiments, the parameters associated with the generated surgical implant 100, and the particular surface topographies of the one or more patient-specific surfaces 110 and 105 are represented by the illustration in FIG. 2 and could be incorporated into the 3D digital representation 740, described in connection with FIG. 7. The exemplary implant 100 can include one or more 3D-printed bodies, which the system can customize for a variety of footprints, heights, and other parameters to accommodate various patient anatomies and provide improved fusion, articulation, and placement of the implant and/or associated fixation devices. For example, as shown in the non-limiting example illustrated in FIG. 2, the system can customize a patient-specific implant 100 to integrate with one or more of the patient's anatomy surfaces 205 to improve osseointegration. In some embodiments, the system generates patient-specific surfaces using artificial intelligence models to customize the patient-specific surface of the implant/device for articulation and mating with another portion of the patient's anatomy.

Figure 3:
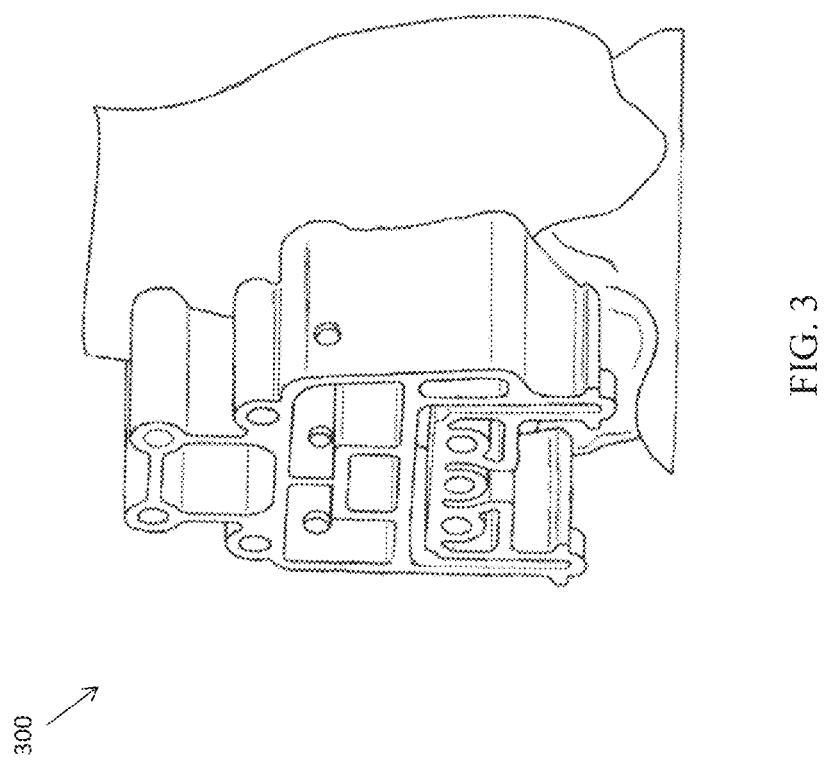
FIG. 3 illustrates an exemplary personalized surgical cut guide generated according to one embodiment of the present disclosure.

FIG. 3 illustrates an example of a personalized surgical cut guide 300 to assist in anatomy removal and in implant placement. In some embodiments, the parameters associated with the generated surgical cut guide 300, represented by the illustration in FIG. 3, could be stored in the implant data 1155 of the memory 730 (see FIG. 11). In various embodiments, the surgical cut guide 300 is generated based on patient-specific anatomy data to provide a customized surface topography that aligns with the curvature of a patient's anatomy to provide for customized implant placement, articulation, mating, and alignment.

Figure 4:
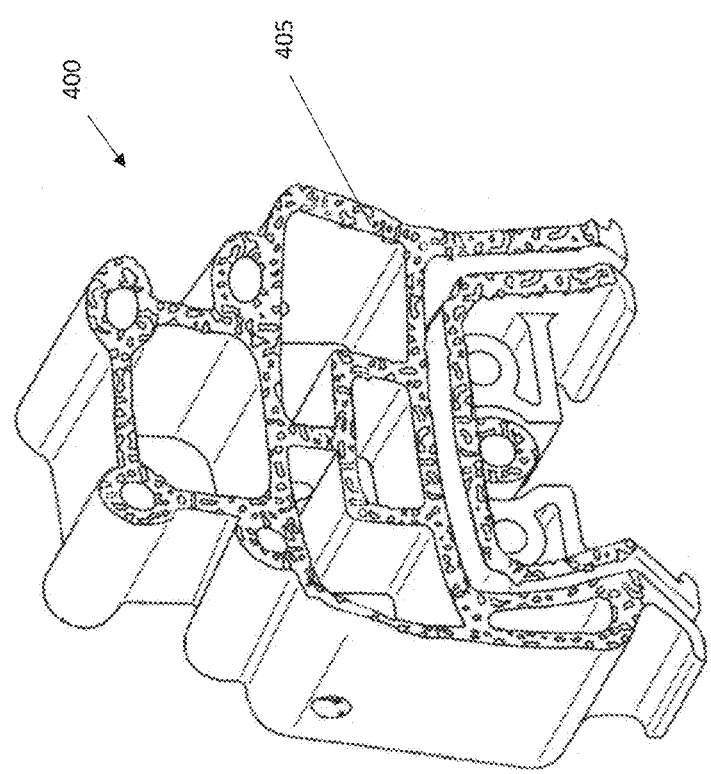
FIG. 4 illustrates an exemplary personalized surgical cut guide with patient-specific surfaces generated according to one embodiment of the present disclosure.

FIG. 4 illustrates an example of a personalized surgical cut guide 400 to assist in implant placement and/or anatomy removal, wherein the surgical cut guide 400 includes one or more patient-specific surface structures 405. In the non-limiting example shown in FIG. 4, a patient-specific surface structure 405 includes a porous (e.g., gyroid or other lattice structure) area. Further details regarding the specifications of the lattice structure 405 can be provided in the form of CAD file 760 (or other suitable type of file or digital representation), described in more detail in connection with FIGS. 7 and 11, for example.

Figure 5:
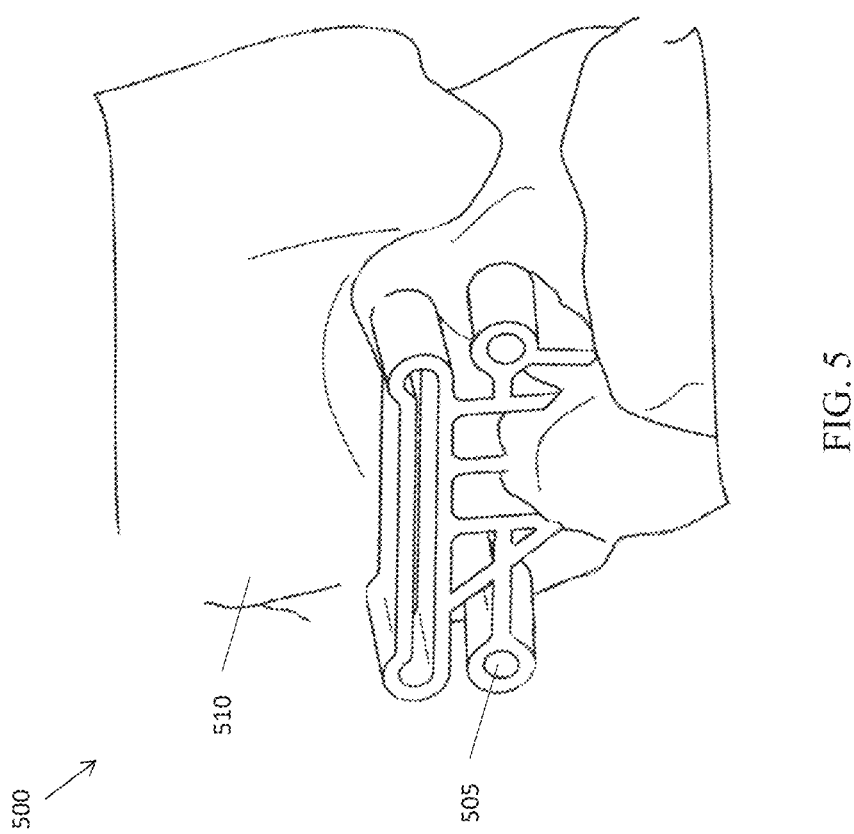
FIG. 5 illustrates an exemplary personalized surgical cut guide generated according to one embodiment of the present disclosure.
Figure 6:
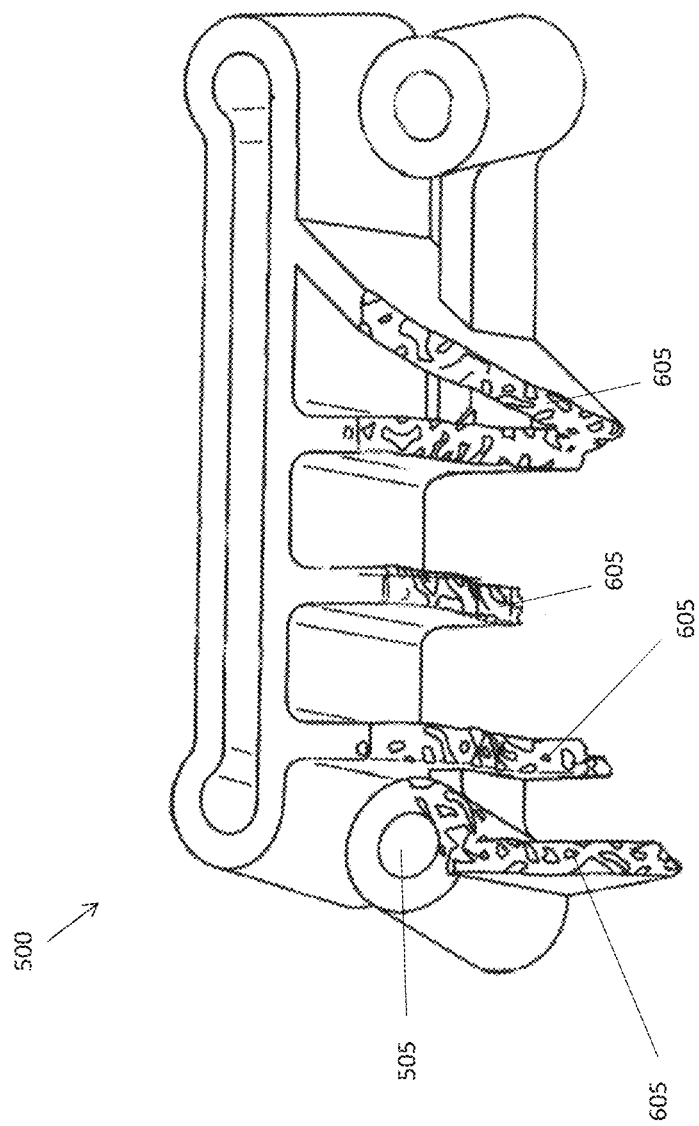
FIG. 6 illustrates an exemplary personalized surgical cut guide with patient-specific surfaces generated according to one embodiment of the present disclosure.

FIG. 5 illustrates an example of a personalized surgical cut guide 500 aligned with a patient's anatomy 510, wherein the surgical cut guide 500 is generated to assist in implant placement and/or anatomy removal, wherein the surgical cut guide 500 includes one or more patient-specific surface structures 605 (see FIG. 6). The personalized surgical cut guide 500 can include, in this example, apertures 505 (e.g., thread holes, pinholes, openings for surgical tools, etc.), as well as a plurality of surfaces and/or topographies.

FIG. 6 illustrates an example of the personalized surgical cut guide 500 of FIG. 5, wherein the surgical cut guide 500 includes one or more patient-specific surface structures 605. In this non-limiting example shown in FIG. 6, the cut guide 500 includes a lattice structure on the patient-specific surface 605. In some embodiments, the system can configure the one or more patient-specific surfaces 605 of the cut guide 500 to improve alignment and friction with the patient's anatomy 510 (see FIG. 5) during a surgical procedure. The personalized surgical cut guide 500 can include apertures 505, as described in connection with FIG. 5. In some embodiments, one or more artificial intelligence models, including but not limited to those described in connection with FIGS. 7 and 13, can determine aperture location, size, and other configuration parameters associated with the personalized implants and/or devices. In some embodiments, the aperture configuration can be determined, at least in part, on the particular implant selected and/or patient-specific anatomy. In some embodiments, the parameters associated with the generated surgical implants, like those shown in the non-limiting exemplary embodiments of FIGS. 1 and 2, and/or the surgical cut guides, like those illustrated in FIGS. 3-6, could be stored in the implant data 1155 of the memory 730 and represented by the patient anatomy representation 740, as described in connection with FIGS. 7 and 11.

Figure 7:
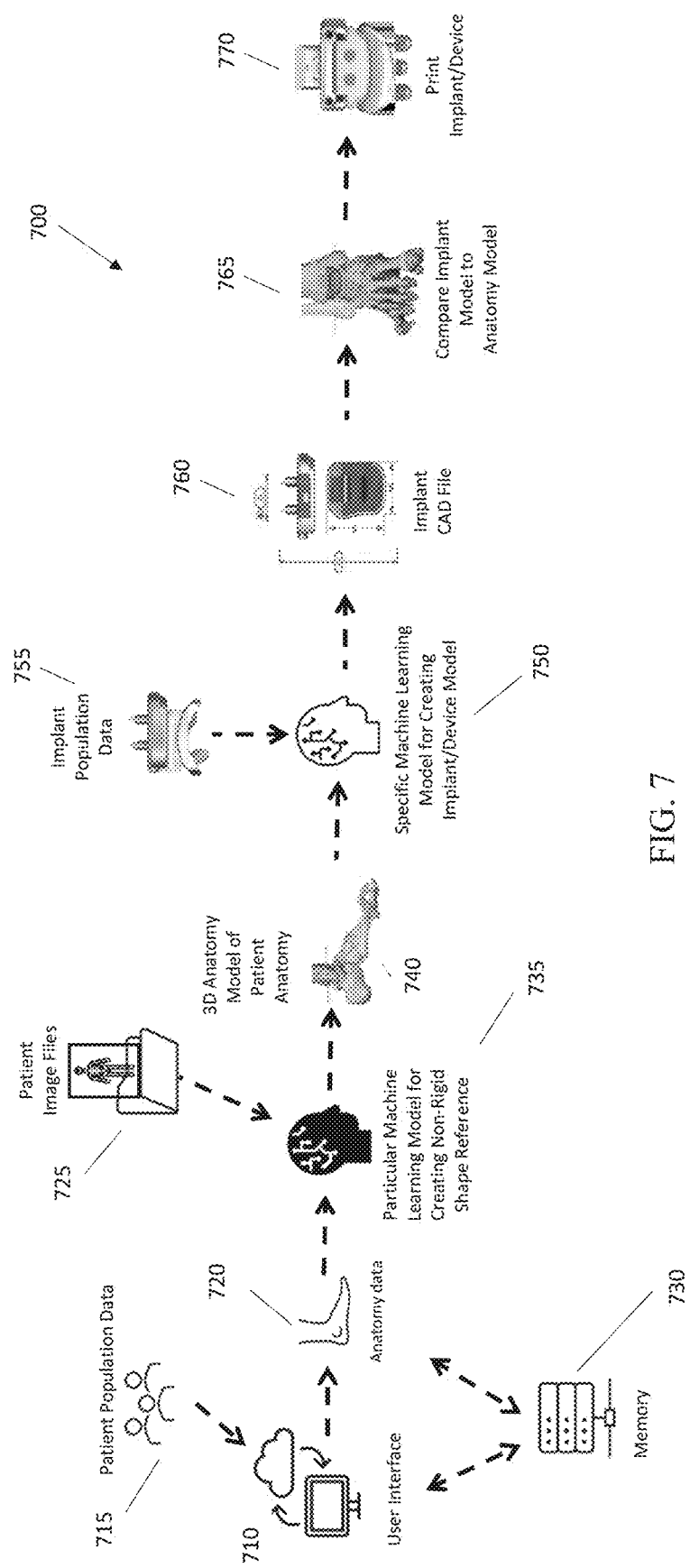
FIG. 7 is a storyboard diagram of a process for generating a personalized surgical implant according to embodiments of the present disclosure.

Exemplary Patient-Specific Device Production Systems and Processes FIG. 7 represents an exemplary overview process 700 for generating personalized surgical implants as described herein, according to embodiments of the present disclosure. As one skilled in the art will understand and appreciate, the generation process overview 700 shown in FIG. 7 (and those of all other flowcharts and sequence diagrams shown and described herein) represents merely one approach or embodiment of the present system, and other aspects are used according to various embodiments of the present system. The steps and processes may operate concurrently and continuously and are generally asynchronous, independent, and not necessarily performed in the order shown.

FIG. 7 is an illustrative overview of an implant generation process 700 to design and generate a personalized surgical implant 765 using one or more trained artificial intelligence models to process patient-specific image files 725 and/or other data and files (e.g., implant data). In exemplary embodiments, the system iteratively trains and utilizes one or more trained models to process patient data, anatomy data, and other data elements to design and generate patient-specific surgical implants/devices based, in part, on a patient's 2D image files. According to some embodiments, the system receives and processes patient population data 715 including information and data related to a plurality of patients. The patient population data 715 can include, among other things, anatomy data 720 comprising anatomical representations of one or more anatomical features for a plurality of patients. In some embodiments, the patient population data 715 can include demographic information, medical history and records, scans and image files, provider remarks, patient notes, appointment history, personal information, and other data elements. In some embodiments, the patient data includes one or more patient image files, which may be medical images of a plurality of file types including, but not limited to: 2D images, 3D images, videos, digital imaging, and communications in medicine (DICOM) files, X-rays, computed tomography (CT) scans, magnetic resonance imaging (MRI) scans, ultrasounds, nuclear medicine imaging, positron-emission tomography (PET), photographs, and other types of medical images and imaging file formats. In some embodiments, these image files are extracted from the patient data or retrieved from other data sources.

In at least one embodiment, the system may process the patient population data 715 to extract anatomy data 720. In some embodiments, the anatomy data 720 can include data elements and information associated with specific patients, specific patient characteristics (e.g., age, medical condition, etc.), specific anatomical features (e.g., body parts), specific anatomy characteristics (e.g., diseased, healthy, etc.), and other parameters. As will be understood, the anatomy data 720 may include one or more features extracted from the patient population data 715 and/or the patient-specific imagine files 725.

Figure 13:
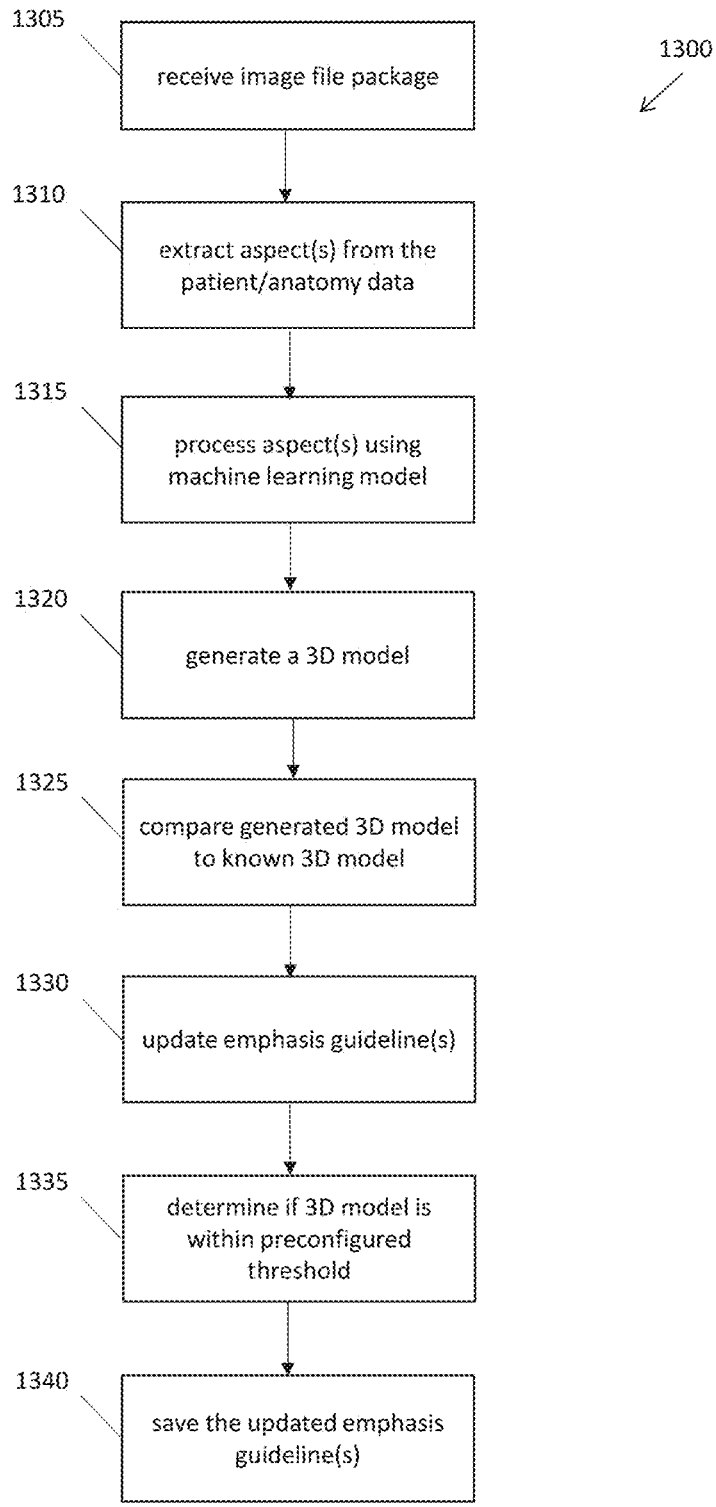
FIG. 13 is a flow diagram of a process for iteratively training an artificial intelligence model according to embodiments of the present disclosure.

The system, in at least one embodiment, may construct and/or train an initial artificial intelligence model 735 based on the received patient population data 715, including, but not limited to, image data and/or extracted feature information from memory 730 (see FIG. 13).

The system can train a particular artificial intelligence model based on the anatomical representations of the image files of existing patient population 715 and anatomy data 720 to generate a non-rigid shape reference to create a 3D digital representation 740 within preconfigured tolerances. The artificial intelligence model training aspects of the system and processes are described in more detail in connection with FIG. 13. According to some embodiments, the system receives patient and/or implant data via the user interface 710 and/or from memory 730 to train the one or more artificial intelligence models (see FIG. 13). As will be understood from discussions herein, the system may receive or retrieve patient data from a variety of other sources, such as, but not limited to, patient records, insurance records, third-party systems or databases, etc.

The system, in at least one embodiment, leverages the trained particular artificial intelligence model to produce one or more 3D digital representations 740 of patient anatomy based on patient image files (e.g., patient-specific image files 725) and anatomy data (e.g., anatomy data 720).

Figure 8:
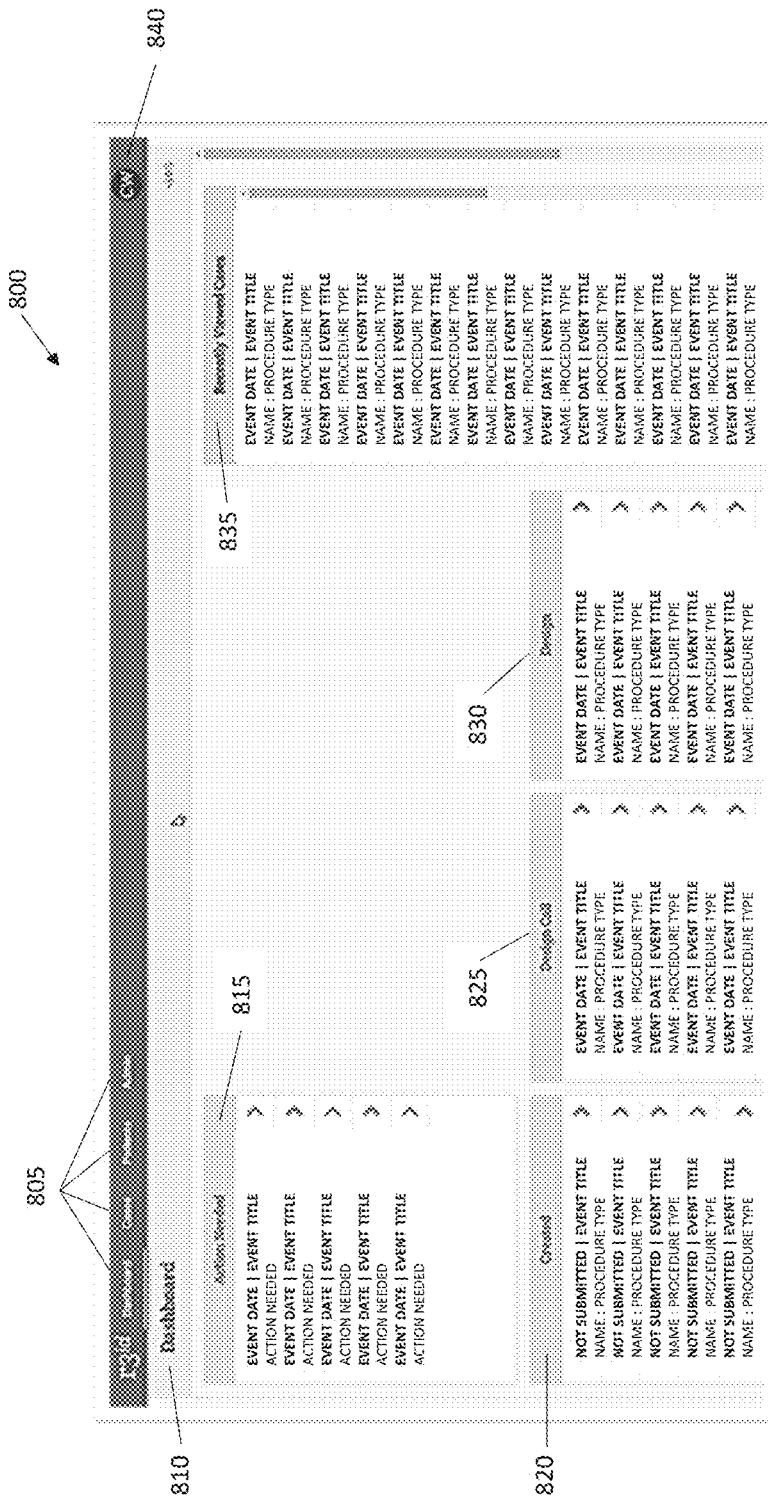
FIG. 8 illustrates a graphical interface display showing a dashboard view designed for a user interface according to embodiments of the present disclosure.
Figure 9:
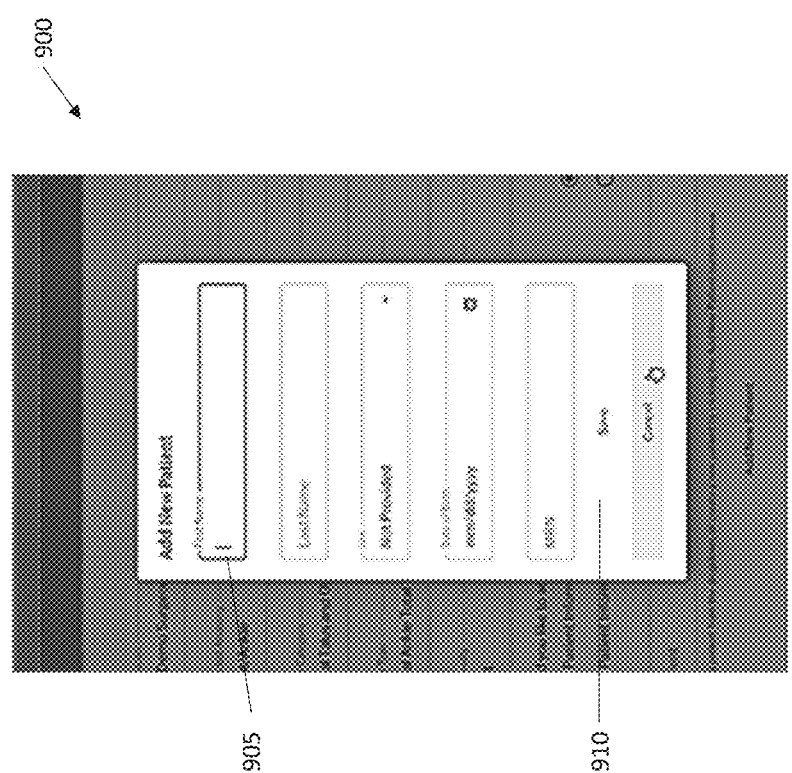
FIG. 9 illustrates a graphical interface display for entering patient data designed for a user interface according to embodiments of the present disclosure.
Figure 10:
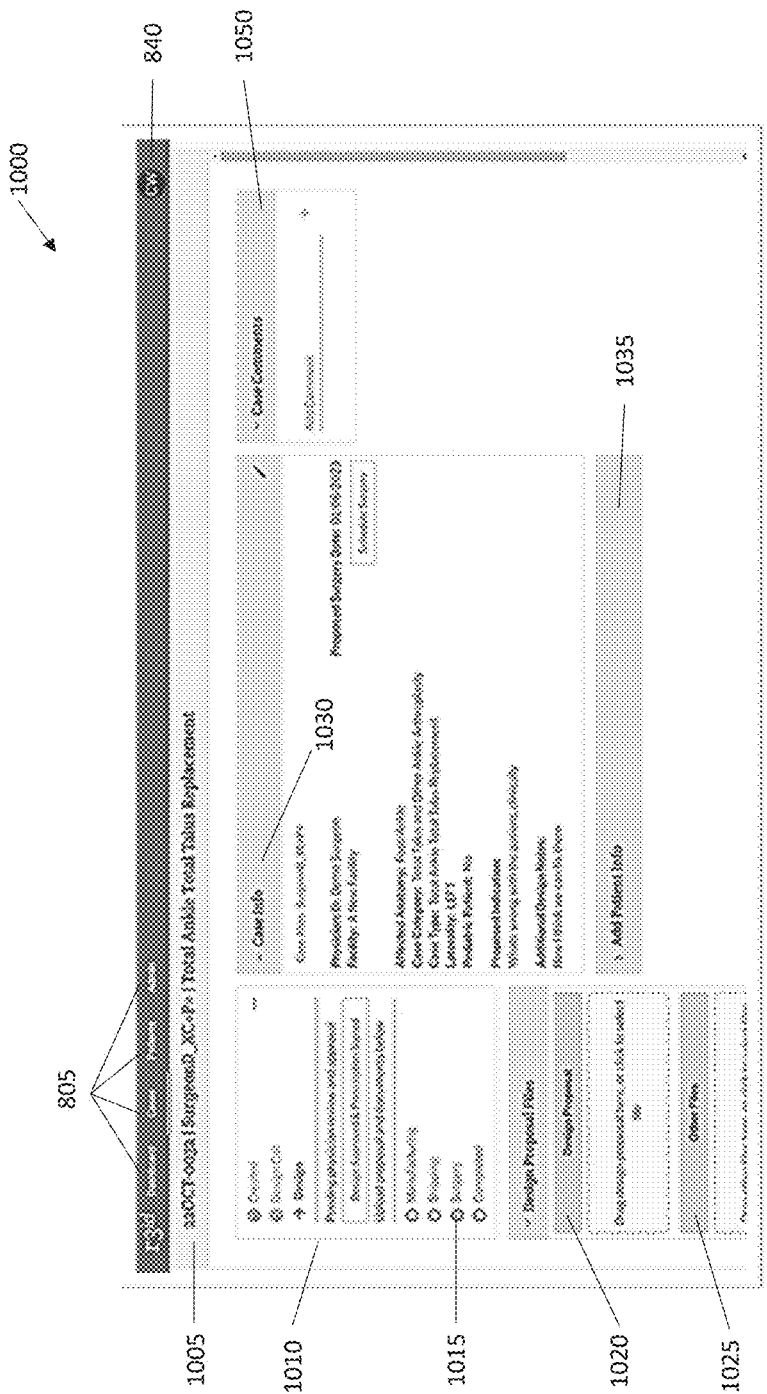
FIG. 10 illustrates a graphical interface display showing an overview of an event associated with generating an implant for a particular patient designed for a user interface according to embodiments of the present disclosure.

In particular embodiments, the system receives 2D patient-specific image files 725 and anatomy data 720 that is specific to the patient, specific patient anatomy, or a particular procedure (e.g., ankle arthroplasty). The system, in at least one embodiment, transforms the 2D patient-specific image files 725 into a digital representation, which is supplied as a data input into the artificial intelligence model. In some embodiments, the digital representation includes a 3D representation. In some embodiments, the user interface 710 is designed to receive data inputs from a user. For example, the user interface 710 can be used to upload patient files for a new patient. Further examples of the user interface 710, in at least some embodiments, are shown in FIGS. 8-10 and are discussed in relation thereto.

In one or more embodiments, the system uses the 2D patient-specific image files 725 and anatomy data 720 as inputs (along with, in at least one embodiment, other data elements) to the trained particular artificial intelligence model 735. In this example, the particular artificial intelligence model 735 extracts one or more features from the 2D patient-specific image files 725 and uses a non-rigid shape reference construct to "fill in" data points not captured in the 2D patient-specific image files 725.

In some embodiments, the trained artificial intelligence model 735 can analyze the contours and/or features of the patient image files 725 and compare those contours and/or features to contours and/or features from image files stored in memory 730 and/or associated with the population data 715 used to train the artificial intelligence model 735. When similar features, aspects, and/or patient-related data elements (e.g., similar injury and/or implant recommendation in physician notes) are identified, the particular training model 735 can use the non-rigid shape references to generate a patient-specific non-rigid shape reference for the particular patient being evaluated. In at least this way, the artificial intelligence model 735 generates a non-rigid shape reference that accurately and efficiently transforms the 2D images into 3D digital representations or anatomy models by filling in gaps in the data elements associated with the patient-specific anatomy that is not shown in the patient-specific image files 725 and may create one or more patient-specific surfaces (e.g., a surface that is not displayed due to the angle or resolution of the image files). In some embodiments, a first aspect may include the anatomy data related to the particular joint, while a second aspect may include patient-related data elements. Other configurations of first and second aspects (and additional aspects) of the patient anatomy data are contemplated within the scope of the present disclosure. In non-limiting embodiments, the system analyzes all relevant data elements associated with an anatomical feature to generate a non-rigid shape reference used with the particular artificial intelligence model to create a 3D digital representations 740 that is patient-specific and fine-tuned based on patient-specific information that may be indirectly related to the particular anatomical feature for which the device is being generated (e.g., medical history, accidents, injuries, medical conditions, etc.). The data analysis and implant generation technique(s) described herein are an improvement over the prior art for many reasons, but at least in that the embodiments described herein do not limit data analysis to the best fit or nearest neighbor techniques and instead intelligently considers all relevant data elements associated with an anatomical feature, including those not directly related in order to design and generate a patient-specific surgical device. It will be appreciated that the data analysis and modeling techniques are not limited to those described in the embodiment described in connection with FIG. 7 and other modeling techniques and analysis processes are contemplated within the scope of the present disclosure.

The generated patient-specific 3D digital representation 740 may represent a calculated approximation at a data representation of the patient's anatomy based on the patient-specific image files 725 and other patient-specific data. In at least one embodiment, the system may generate the 3D digital representation 740, which may be an anatomy model based on a patient-specific surface or anatomy data representation including the non-rigid shape reference. For example, in a certain embodiment, the system may combine a surface from the non-rigid shape reference artificial intelligence model 735 that corresponds to a surface of patient anatomy (e.g., a surface of a patient's tibia) with a general anatomical feature shape. As shown in the embodiment in FIG. 4, the patient-specific surface 405 may substantially mirror a patient-specific surface of the non-rigid shape model 735 and the system may add the remaining structure of the device 400 to the patient-specific surface 405.

In various embodiments, the system may automatically (or semi-automatically) adjust the patient-specific surface from the non-rigid shape reference created by the particular artificial intelligence model 735 for the 3D digital representation 740. In one embodiment, the system may automatically add an offset or depth to the patient-specific surface (e.g., a depth for porosity or the like) for the 3D digital representation 740. As such, as will be understood from discussions herein, patient-specific surfaces of 3D device models may or may not exactly match patient surfaces determined by the non-rigid shape model 735 or the patient-specific image files 725. In various embodiments, the created 3D digital representation 740 can serve as the basis for a CAD implant file 760 and a 3D device model 765.

In at least one embodiment, the system uses the patient-specific anatomy model 740 or an extracted portion thereof, such as, for example, a patient-specific surface, as an input into a second artificial intelligence model (sometimes referred to herein as a "specific" artificial intelligence model) for creating a patient-specific device (e.g., implant, surgical guide, instrument, etc.). In some embodiments, in system leverages the patient-specific 3D digital representation 740 and other patient data (e.g., medical history) is an input to the trained specific artificial intelligence model to generate a device CAD file 760. In some embodiments, the artificial intelligence model generates a digital representation of the patient-specific device. In at least one embodiment, the iteratively trained learning model 750 is trained on implant population data 755 including data elements associated with implants designed and created for numerous patients, as stored in memory 730 and/or in the patient population data 715, as described in more detail in connection with FIG. 13. In various embodiments, the implant generation process 700 further includes analyzing the surface structure details and other 3D digital representation features including in the patient-specific 3D digital representation 740 to generate an implant CAD file 760 used to print a personalized surgical implant/device 770. In some embodiments, the implant CAD file 760 is provided in the form of a digital representation of the personalized surgical implant/device 770.

It will be understood that printing an implant/device 770 can include any patient-specific instrument, including but not limited to a 3D-printed body. In some embodiments, the system can 3D print the implant/device or may use other manufacturing techniques to create the implant/device. In some embodiments, the output of the implant generation process 700 can include non-surgical implants, medical devices, or other objects or materials. In various embodiments, the 3D-printed body can be constructed from a metallic material (e.g., medical grade titanium alloy), although other constructions and material types are contemplated within the scope of the present disclosure. Additional details associated with embodiments of the implant generation process 700 are described in connection with the flow diagrams of FIGS. 12 and 13.

A non-limiting illustrative example of the above-described process overview shown in FIG. 7 is provided herein before describing the system components and process steps in more detail below. In a non-limiting example for illustrative purposes only, a patient needing surgery to replace a portion of their ankle can benefit from the advanced implant generation process 700. For example, the system may receive patient anatomy data, 2D image files of the exemplary patient's ankle, and other medical data relevant to the exemplary patient's injury, medical history, and anatomy. As will be understood from discussions herein, the patient anatomy data and/or 2D image files do not include data for every anatomical surface, joint structure, etc. The system can iteratively train an artificial intelligence model, or select a trained artificial intelligence model, based on anatomy data 720 related to the ankle from the patient population data 715. In some embodiments, the artificial intelligence model 735 can include a particular artificial intelligence model. The particular artificial intelligence model can use, at least in part, a non-rigid shape reference to generate missing 3D data points and/or silhouettes from the 2D image contours of the patient-specific image files 725 in order to generate a 3D digital representation 740 of the patient's ankle. In some embodiments, the 3D digital representation 740 includes patient-specific surfaces for the different features and/or aspects of the patient's ankle based on the patient-specific image files 725 as processed by the trained artificial intelligence model 735.

In various embodiments, the system can process the 2D patient-specific image files 725 using a segmentation process to generate the 3D digital representation 740 of the patient anatomy. In some embodiments, the segmentation process can be executed using the one or more trained artificial intelligence model 735. In some embodiments, the 3D digital representation 740 is transformed into a point cloud space and is input into the trained artificial intelligence model 735 to perform a registration and/or alignment of the point cloud space (e.g., a non-rigid or rigid point cloud registration). In various embodiments, the registration and/or alignment of the point cloud space can be input into the trained artificial intelligence model 735 with patient image files 725 and/or other patient population data 715.

In some embodiments, the output of the artificial intelligence model 735 can include a lower dimensional representation of the patient anatomy, which is combined with patient-specific surfaces to create a patient-specific device 770. In some embodiments, the patient-specific surfaces generated are based on the output of the trained artificial model 735 applied to the lower dimensional representation of the patient anatomy. In some embodiments, the process of generating patient-specific surfaces can be performed by a separate trained artificial intelligence model.

Further, in the non-limiting illustrative example, a second artificial intelligence model 750, a specific artificial intelligence model in some embodiments, is used to create a CAD file 760 (or other digital file) for a custom implant (in some embodiments, this can be integrated into the same artificial intelligence model 735 used to generate the 3D digital representation 740). In some embodiments, the specific artificial intelligence model 750 is trained based on implant population data 755, including details and designs for many (e.g., hundreds or thousands of) surgical implants and devices created for a plurality of patients, including details related specifically to ankle implants, in this non-limiting example. The patient-specific 3D digital representation 740 of the patient's ankle, including the patient-specific surfaces generated based on the patient image files 725 is an input to the trained implant/device artificial intelligence model 750 to develop an implant personalized to the patient's ankle anatomy. In at least this way, the specific artificial intelligence model 750 takes population data of all ankle implants and ankle implant-related devices (e.g., cut guides) designed for a plurality of patients and generates an implant design customized for the patient using all relevant data elements (e.g., surgeries, disorders, similar features/parameters/aspects of the population data information and the patient-specific information) to generate a CAD file 760. In some embodiments, the system creates a 3D implant model 765 from the generated CAD file 760 and compares the 3D implant model 765 to the patient's 3D digital representation 740 before printing (or otherwise generating) the patient-specific implant/device 770.

In this illustrative example, the system designs a custom ankle implant, and then the 3D device model of the ankle implant is generated and digitally modeled (or physically modeled) in the patient's anatomy model to ensure an accurate fit. After a design engineer and/or provider has approved the proposed design, or the advanced model has performed a verification/validation process, the system prints or otherwise creates the custom implant and/or device for the patient's ankle surgery. It will be appreciated that this example is merely illustrative, and the system and processes described herein can be applied to other anatomical features, surgical procedures, devices, etc.

In some embodiments, the implant generation process 700 can be executed via a computing environment (not shown), which can be provided in the form of one or more computing devices, server banks, computer banks, or other arrangements. For example, the computing environment can include one or more computing devices that together may include a hosted computing resource, a grid computing resource, and/or any other distributed computing arrangement. The computing environment can further include one or more routers. In some cases, the computing environment can correspond to an elastic computing resource where the allotted capacity of processing, network, storage, or other computing-related resources may vary over time. In some embodiments, the computing environment can also include an elastic cache designed to scale and adapt based on system demands and available capacity.

FIGS. 8-10 illustrate various visual graphics 800, 900, and 1000 that can be generated on the one or more user interfaces 710 and used to facilitate the implant generation process 700. Referring to FIG. 8, the visual graphic 800 can correspond to an interactive dashboard 810 function of the implant generation process 700. As an example, the visual graphic 800 corresponds to a dashboard for an internal user like a design engineer or system engineer, as non-limiting examples. The visual graphic 800 can also include tabs 805 or navigation links to other screens or visual graphics (not shown).

In some embodiments, the dashboard 810 can include a list of action items 815 assigned to the particular user 840 logged into the dashboard 810. In some embodiments, for example, if the user is a system administrator, team lead, or similar role, the dashboard may include all action items 815 assigned to all users with access to the system or platform. In some embodiments, the action items 815 and associated fields can be edited from the dashboard 810. In some embodiments, the dashboard 810 can further include a list of created events 820. For example, the name field associated with an event can include one or more fields for the patient name, surgeon name, the name of the user who created the event, the user assigned to the next steps for the event, etc. In some embodiments, the created event 820 list includes new implant requests that have been created but have not been submitted to the design team.

In some embodiments, after a new implant request or other created event 820 has been submitted for design, a design call 825 is generated. In one non-limiting example, the design call 825 can include a schedule function to coordinate a meeting between the provider and one or more design engineers to review the details, recommendations, and other strategy items or considerations before the design team creates a design proposal. In some embodiments, after the design call, 825 is complete, the system can generate a design 830 event until the design engineers have submitted a design proposal for the implant. In some embodiments, there may be a history 835 window that shows a user's recently viewed events. In some embodiments, the history 835 window is updated according to when another user accesses an event.

In some embodiments, the display configuration of the user interface 710 may be modified based on a particular user's function or access level. For example, the dashboard 810, screens, windows, options, and accessible data may populate differently for a user who is logged in as an external provider than it would appear for a user logged in as an internal design engineer. In this embodiment, the internal design engineer is used as a non-limiting example but can include other internal-facing user roles. Other internal-facing user roles can include but are not limited to, the commercial team, customer service, design engineers, design leads, regulatory, and system administrators. As used throughout the disclosure, the "provider" can include but is not limited to, a clinical staffer, physician, members of the surgical team, etc. There may also be additional user roles, functions, or permission levels based on required training (e.g., HIPAA training). For example, users that have received HIPAA training may be able to access and view all details of patient data, whereas someone without HIPAA training would only have access to view de-identified patient data and image files, including where all patient information and personal identifying information has been removed.

In some embodiments, the user interface 710 can include one or more interactive interfaces to display customized information and requests based on the permissions and access level of a particular user. When a particular user logs in via an authentication process, the system can identify the access level associated with the user. In some embodiments, the user interface 710 can include a plurality of tabs, screens, windows, menus, and other options designed to receive input. In one example, the user interface 710 can include, but is not limited to: an interactive dashboard with pre-configured fields to accept a new case with an implant request, modify the request submissions, view request submissions and status, input patient data and upload patient files, and generate design proposals and manufacturing requests. Continuing with this particular example, the user interface 710 communicates with the memory 730 to retrieve and package a plurality of data elements via an API associated with the particular access level associated with the user. Examples of the plurality of user interfaces 710 associated with the different access levels may include but are not limited to, the interface graphics as seen and described in connection to FIGS. 8-10.

It will be understood that the user interface 710 can be used for other interactions with patient population data 715, patient-specific image files 725, data elements, and similar aspects of the disclosed system and processes including, but not limited to importing, editing, or modifying, viewing, exporting, linking, or other interactions. The user interface 710 can be integrated with a plurality of third-party applications and utilize a network 1170 or cloud-based servers to provide seamless synchronization among the components of the system throughout the implant generation process 700. In one example, if a user starts a new request using a user interface 710 that is web-based, and then wants to complete the request using a user interface 710 on a mobile device, the system can utilize a synchronized data storage solution to synchronize the user interfaces 710. In some embodiments, the authentication process can identify that the same user is accessing a request, and the system can retrieve the data elements associated with the request and send the plurality of data elements via an API to the user interface 710. The authentication process is described in more detail in connection with FIG. 11.

FIG. 9 illustrates a visual graphic 900 corresponding to adding a new patient. In some embodiments, the visual graphic 900 may populate as a preliminary step when creating a new request or event associated with generating a surgical implant. As shown in FIG. 9, the visual graphic 900 may include one or more textbox 905 designed to receive user input. In some embodiments, the textbox 905 may be provided in the form of a selection menu of pre-generated options. After the textbox 905 information is completed, the user 840 can select save 910 and the system can store the patient data in the memory 730 of the generation system 1100, as described in more detail in connection with FIG. 11. In some embodiments, the system 1100 can recognize that the new patient data entered through the user interface 710 matches patient data already saved in the memory 730. In this example, the system 1100 can synchronize the new patient data with the existing patient data rather than generating a duplicate patient entry.

FIG. 10 illustrates a visual graphic 1000 corresponding to an interactive user interface 710 for an event. In one embodiment, the event label 1005 can include the information shown on the dashboard 810 as shown in connection with FIG. 8. In some embodiments, the event label 1005 shown in the visual graphic 1000 may include more details than what is visible from the dashboard 810.

In some embodiments, the event visual graphic 1000 may include a timeline 1010 to track the status of the event. In this example, different graphics or visual indicators 1015 can be used for events that are complete, in progress, or completed. In some embodiments, the timeline 1010 may include information as to the user who has been assigned a task associated with the event. In some embodiments, the event can include a design proposal file upload 1020. In some embodiments, the design proposal may include a personalized implant design generated by the processes and systems described herein and submitted for provider approval. Additional file upload options 1025 can also be included on the visual graphic 1000.

The event visual graphic 1000 can further include event details 1030. The event details 1030 can include but are not limited to, patient data, anatomy data 720, image data 1150, implant data 1150, CAD model data 1160, and other data, like the provider information, the facility information, the proposed surgery date, etc.

The event visual graphic 1000 can also include patient data, depending on the access level associated with a user 840. There can also be a comment field 1050 where one or more users interacting with the event can add remarks or notes. As described in connection with FIG. 8, the visual graphic 1000 may include one or more tabs 805 or navigation links to other screens or windows and the visual graphic 1000 may be configured based on a particular user 840 access level or permissions.

It will be appreciated that the fields and options associated with each aspect of the visual graphics 800, 900, and 1000 are not limited to those shown in the visual graphics 800, 900, and 1000. In at least this way, the system can customize user interface(s) 110 according to the particular user, system, process, application, etc.

Figure 11:
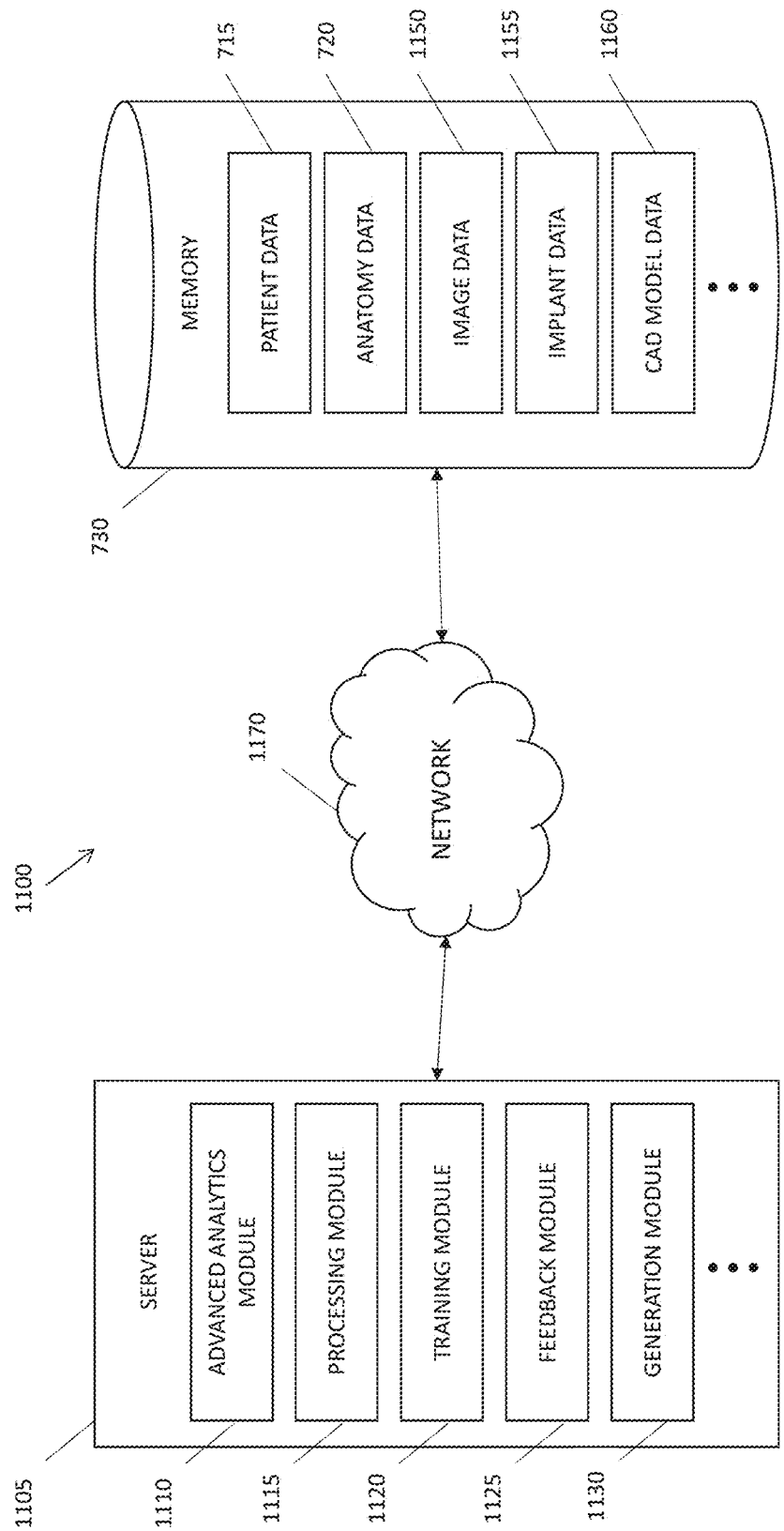
FIG. 11 is a system diagram of a system architecture according to embodiments of the present disclosure.

FIG. 11 is a block diagram of an implant generation system 1100 that can be used to execute the implant generation process 700, in some embodiments. The system 1100 can include a server 1105, one or more programmable processors and memory units 730, and one or more network interfaces 1170. In some embodiments, the one or more programmable processors and memory units 730 can be integrated into one or more of the other system 1100 components including but not limited to, the server 1105 and/or network interface 1170.

While the system components described include a server 1105 and a network interface 1170, it will be recognized by one skilled in the art that the system configuration could include a plurality of computing devices in various configurations. The computing elements of the system 1100 can be provided via one or more computing devices that may be arranged, for example, in one or more server banks, computer banks, or other arrangements. Such computing devices can be located in a single installation or may be distributed among many different geographical locations. For example, the system 1100 can include computing devices that together may include a hosted computing resource, a grid computing resource, and/or any other distributed computing arrangement. The computing devices can further include one or more routers. In some cases, system 1100 can correspond to a dynamic computing resource where the allotted capacity of processing, network, storage, or other computing-related resources may vary over time.

In one embodiment, the implant generation system 1100 is designed to process data elements using a plurality of data processing modules within the server 1105. The system 1100 server 1105 can include: an advanced analytics module 1110, a processing module 1115, a training module 1120, a feedback module 1125, and a generation module 1130. In some embodiments, the system 1100 may include additional modules for processing and analyzing different data elements and data sets. As will be understood from discussions herein, the plurality of data processing modules shown in FIG. 11 is exemplary. The system 1100 may include any suitable number of processing modules (including a single processing module) for executing or carrying out any of the processes discussed herein. It will be appreciated that the training module 1120 can be provided in the form of the one or more training models discussed throughout the present disclosure, including but not limited to the particular artificial intelligence model 735 for generating a non-rigid shape reference, the specific artificial intelligence model 750 for generating a 3D device file and/or test implant, and/or the ensemble artificial intelligence model comprising both the particular artificial intelligence model 735 and the specific artificial intelligence model 750. It will be appreciated that where used herein, "3D device file" can include a 3D implant file or other suitable file for generating a medical device or instrument.

In some embodiments, the data elements can include patient population data 715, patient-specific data (not shown), anatomy data 720, image data 1150, implant data 1155, and CAD model data 1160. It will be understood that the data elements can include other data and are not limited to the embodiment(s) shown or described in connection with FIG. 11.

In one or more embodiments, the system 1100 received transmitted data including patient data, which, as described in connection with FIG. 7, can include but is not limited to, medical history and records, scans and image files, provider remarks, patient notes, appointment history, personal information, and other data elements. In some embodiments, the patient data can include additional information that may impact the generation of a personalized implant (e.g., height, weight, gait, surgical history, injuries, accidents, deformations, disabilities, mobility, etc.). In some embodiments, the patient data can be included in the patient-specific image files 725.

In some embodiments, the system 1100 receives transmitted or extracted data including anatomy data 720. As described in connection with FIG. 1, the anatomy data 720 can include data elements and information associated with specific patients, specific anatomical features, specific characteristics, and other parameters. In some embodiments, the anatomy data 720 associated with specific patients can include measurements of anatomical features, which can be automatically determined by the system and processes described herein and/or recorded manually by a provider or similar. In some embodiments, the measurements may include not only the anatomical feature being evaluated for the implant generation process but can also include adjacent anatomical features including but not limited to, adjacent joints, surfaces, or portions thereof. In some embodiments, the anatomy data 720 associated with specific patients can further include patient population data 715 and extracted data elements related thereto, such that the evaluation of the patient's anatomy data may be impacted by the relevant patient population data 715. As a specific non-limiting example, if a patient has had Tommy John's surgery from a prior baseball injury, as indicated in the patient data, this data will be evaluated by the system during the analytics process(es) described herein, and additional anatomy data 720 may be extracted and/or considered for generating an implant for a shoulder replacement, including but not limited to training and/or tuning the artificial intelligence model based on patient population data 715 for other patients that have had Tommy John's surgery.

In some embodiments, the anatomy data 720 associated with specific anatomical features can include data about a particular body part (e.g., left foot) or portion thereof (e.g., left ankle, or a segment of the left ankle joint). The anatomy data 720 associated with specific anatomical features can include data elements and information about the specific anatomical feature being evaluated from not only the particular patient being considered but also the specific anatomical feature from the entire patient population data 715 and anatomy data 720 database. Similar to the example above, this information can include data elements related to other anatomical features that may impact the specific anatomical feature being replaced or modified with a surgical implant.

In some embodiments, the anatomy data 720 associated with specific characteristics can include healthy, diseased, deformed, injured, or similar characteristics that may impact the size, shape, measurement, surface, mobility, etc. of a particular anatomical feature. In some embodiments, the specific characteristics can include a plurality of disease states, the change to a specific anatomical feature over a healing process or over time as a patient ages, or similar variations of a specific anatomical feature over a period of time. The anatomy data 720 can further include other parameters or metrics associated with the anatomical feature(s) of a plurality of patients and for the particular patient being evaluated.

In some embodiments, the system 1100 receives transmitted or extracted data including image data 1150. In some embodiments, the image data 1150 can include the patient-specific image files 725 described in connection with FIG. 7. The image data 1150 can further include data elements extracted from the patient-specific image files 725. For example, the image data 1150 can include the measurements for a specific anatomical feature described in connection with the anatomy data 720. The image data 1150 can also be used for object detection and other image processing techniques to extract and analyze data according to the processes described herein. The image data can also include date information related to when the image was taken. In some embodiments, the date information can be used to track or analyze change(s) to a specific anatomical feature over time. In one non-limiting example, this can include analyzing the change to a first anatomical feature after a period of time when an injury occurred to another anatomical feature.

In some embodiments, the system 1100 receives transmitted or extracted data including implant data 1155. The implant data 1155 can include any details needed to generate the personalized implant. In some embodiments, the implant data 1155 can include one or more implant files associated with a particular patient or plurality of patients, including but not limited to the implant population data 755, described in connection with FIG. 7. In some embodiments, the implant data 1155 can also include but is not limited to, surfaces, textures, roughness, pore structures, thickness, ingrowth, holes or apertures, screws or other fasteners, ligaments or other connecting or adjacent anatomical features, lattice structures, dimensions, materials, alignments, cuts, mounting configurations, geometries, correction angles, threads, etc. In some embodiments, the implant data 1155 can include information extracted or stored from previous implants already created and saved in the memory 730.

In some embodiments, the system 1100 receives transmitted or extracted data including CAD model data 1160. The CAD model data 1160 can include but is not limited to the technical drawings generated that are used to print, manufacture, or otherwise generate the surgical implant. In some embodiments, the CAD model data 1160 may include information and data from the implant data 1155. The CAD model data 1160 may also include product code(s), part number(s), stock keeping number(s) (SKU), text to be printed on the implant, project information, other patient information, tolerances, specifications, measurements, notices, instructions, manufacturing directions, provider notes, design engineer remarks, and other details to represent the implant to be printed, created, manufactured, or otherwise generated. In some embodiments, the memory 730 can include other data elements than those shown in FIG. 11 and described above.

In various embodiments, the implant generation process 700 and the implant generation system 1100 can include one or more processes that may be executed via a network interface 1170 designed to perform one or more processes for advanced data processing and transforming data for executing a generation model to create one or more models and/or design files. The networked interface 1170 may include a networked system provided in the form of a computer architecture system provided in the form of various computing components designed to communicate over a network. The network interface 1170 includes, for example, the Internet, intranets, extranets, wide area networks ("WANs"), local area networks ("LANs"), wired networks, wireless networks, cloud networks, or other suitable networks, or any combination of two or more such networks. For example, the network 1170 can include satellite networks, cable networks, Ethernet networks, and other types of networks. In one embodiment, the network interface 1170 is an isolated private network utilizing a private IP address and limiting access to the network.

In one or more embodiments, the system 1100 may also include an authentication service, a notification queue, and a regulatory assessment. The system 1100 can be designed to communicate with and integrate with a plurality of third-party applications. In some embodiments, the authentication service can confirm the identity and user by one or more validation techniques. In one or more embodiments, the authentication service may use, as non-limiting examples: a username and password, personalized token, personal identification number, or biometric data to validate system access associated with a particular account. The authentication service can also be designed to associate a unique identifier for each user, wherein the unique identifier can be used throughout the systems and processes described herein. The unique identifier can be used to indicate the specific access level assigned to a particular user.

The notification queue can be an application for creating, modifying, and logging events, requests, tasks, and action items. The notification queue can also generate, update, and push notifications to one or more devices or applications, including the user interface 710, in some embodiments. In various embodiments, the notification queue is designed to be dynamic, scalable, and integrated with a plurality of third-party applications. In some embodiments, the notification queue is designed to receive data elements from a plurality of data sources or applications and handle the notification generation and management for the plurality of data sources and/or applications. The notification queue can be further designed to create and monitor new events, wherein each event is assigned a unique identification tag and time stamp. Each event can have one or more tasks assigned, each with an individual status, time stamp, and identification. A notification status can be updated automatically in response to receiving user input or other indications that an event has been modified, completed, or assigned to another user.

In some embodiments, the systems and processes herein store and index data from data sources, in a variety of formats, and then use processes for validating and transforming the data to generate CAD files or 3D device models and personalized surgical implants.

In at least one embodiment, the system is designed to automatically (or in response to an input) collect, retrieve, or access a plurality of data elements, including patient data and image files, from one or more patient databases. In some embodiments, the plurality of data elements can include data from a large number of sources and patients with varying data types and formats. In various embodiments, the system is designed to automatically analyze, validate, and index data to facilitate evaluating a plurality of aspects and/or characteristics between a plurality of data elements and data elements associated with a particular patient.

The plurality of data elements may be stored in a dynamic database that utilizes a plurality of modules. In some embodiments, the dynamic database can be provided in the form of the memory 730, be integrated with the memory 730, and/or be connected to the memory 730. The system can be designed to request and synchronize data among and between a plurality of modules. In at least this way, the system is flexible, scalable, and efficient at processing a growing number of data elements related to one or more aspects and/or characteristics. In some embodiments, the system utilizes an advanced generation model to process the output of one or more iteratively trained learning models and create a 3D digital representation, a 3D device model, a CAD file, and/or a surgical implant. In one or more embodiments, the present system can create or otherwise generate a personalized surgical implant using 3D printing techniques.

In one or more embodiments, the present system may transform the plurality of data elements for analysis via the training model processes and other techniques described herein. In at least one embodiment, the present system may clean and transform data to remove, impute, or otherwise modify missing, null, or erroneous data values. In various embodiments, the present system may remove identifying information in order to anonymize and remove any correlated data. Similarly, the system may index and correlate specific data elements, data types, and data sets to facilitate the implant generation process. In at least one embodiment, the system may include data elements from a plurality of patients to create a dynamic database and one or more trained artificial intelligence training models. In certain embodiments, the system may include one or more algorithms to automatically update and train the database and/or training models. For example, in some embodiments, data corresponding to the various aspects of an anatomical feature can be processed with the one or more algorithms to generate parameter values determined from analyzing all the data elements within a database. In various embodiments, the system may include an interface for operating and controlling the various facets of the system and processes as described herein.

Figure 12:
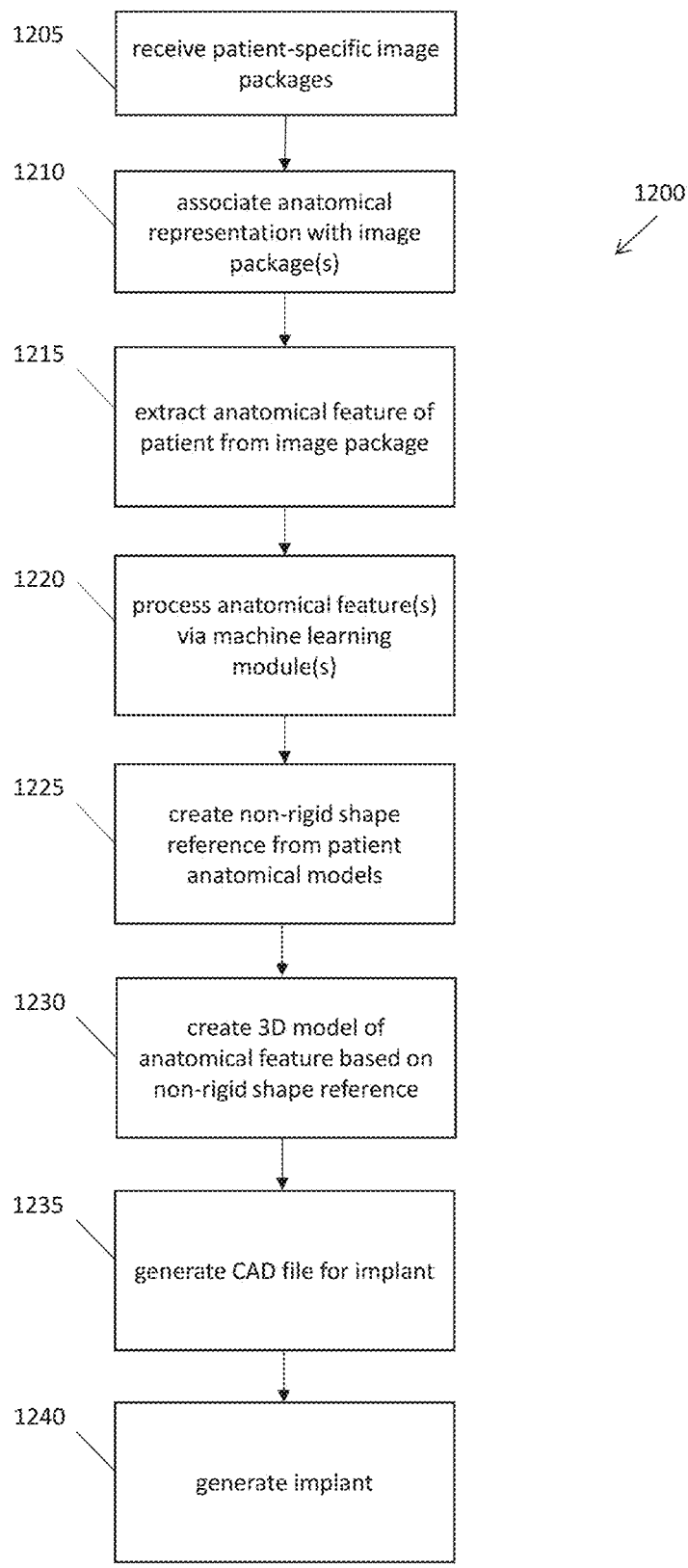
FIG. 12 is a flow diagram of a process for processing patient image files to create a personalized surgical implant according to embodiments of the present disclosure.

FIG. 12 illustrates a process 1200 for processing patient data to generate an implant according to embodiments of the present disclosure. At step 1205, the system receives a patient-specific image package. In some embodiments, the patient-specific image package may include a plurality of patient-specific image files 725. In a non-limiting example, the patient-specific image files 725 can include DICOM files, but can also include various image file types, for example, those described in connection with FIG. 7. In some embodiments, the patient-specific image package is an upload of image or scan files associated with a particular patient and can include a 2D image package. In some embodiments, the 2D image package can include patient-specific anatomy data 720. In some embodiments, the 2D image package can include one or more series of patient-specific image files 725 including 2D image files of patient-specific anatomy. In this embodiment (and others), the series of patient-specific image files 725 are intended to be used together. For example, a series of patient-specific image files 725 may include multiple 2D images of the same anatomical feature (e.g., left ankle). In this example, the series of patient-specific image files 725 is intended to be processed and evaluated together as a complete evaluation of the left ankle from multiple viewpoints and angles.

As discussed herein, the system may receive the patient-specific image packages from one or more sources. In at least one embodiment, the system receives the patient-specific image packages from a user interface 710, such as the user interface 710 discussed in relation to FIGS. 7-10. In some embodiments, the system receives the patient-specific image packages from a mobile application, third-party computing system (e.g., automatically from a CT or MRI system or hospital or clinic image management system), or other suitable source.

At step 1210, the system can associate an anatomical representation with the image packages received at step 1210. In some embodiments, the anatomical representation may include a digital twin or a genetic digital twin. In one non-limiting example, the digital twin can be updated and modified with data over a period of time or as the patient ages. In at least this way, the anatomical representation associated with the image packages can include and incorporate data elements associated with patient population data 715, patient-specific patient data, and anatomy data 720, as described in connection in more detail with FIGS. 7 and 11. In some embodiments, the system can store changes or updates to the digital twin or other anatomical representation in blockchain or other sequential storage systems. In some embodiments, the anatomical representation can include one or more anatomical models from other patients of the patient population data 715 that are stored in the memory 730. In some embodiments, the system can index, prioritize, tag, (or similar), the anatomical representations in step 1210 to prepare for the advanced processing at step 1220. In some embodiments, the anatomical representations can include healthy and diseased anatomical models or other characteristics of anatomy data as described in more detail in connection with FIG. 11. In some embodiments, the anatomical representations can include surface representations, CAD model representations, models, 2D representations, 3D representations, and other types of anatomical models associated with a plurality of patients.

At step 1215, the system can extract data associated with one or more anatomical features corresponding to a particular patient, including but not limited to the anatomy data 720. At step 1215, the process can further include extracting measurements or other information from the image package(s). In some embodiments, the information extracted at step 1215 may include information related to anatomical features on the other side of the patient or with other patients. For example, at step 1215, the process may include extracting information regarding a patient's left knee, which is scheduled to be replaced. In this non-limiting example, at step 1215, the process could also extract information from the left knee of other patients as stored in the image files of the patient population data 715. In some embodiments, the system trains the particular artificial intelligence model using patient population data 715. In one non-limiting example, the system creates a non-rigid shape reference based at least on portions of extracted anatomical left knee data and information from the patient population data 715. In this non-limiting example, the trained particular artificial intelligence model extracts information related to the patient's knee from the patient-specific image files 725 and uses the non-rigid shape reference generated with the particular artificial intelligence model 735 to create a patient-specific 3D digital representation 740 from the patient-specific 2D image files 725.

Additionally, the system could also extract information related to the patient's right knee and information related to the right knees of all other patients in the patient population database 715. In at least this way, the system and processes described herein extract and evaluate all known data elements that may be relevant to the design of the patient's 3D digital representation and/or surgical implant model and/or 3D device model.

At step 1220, the data elements can be processed using advanced artificial intelligence processes. In some embodiments, there may be multiple artificial intelligence models utilized in step 1220. In one non-limiting example, each anatomical feature may be processed by a different machine-learning model. At step 1220 the process can also be configured to generate, train, and execute a plurality of nodes, neural networks, gradient boosting algorithms, mutual information classifiers, random forest classifications, and other machine learning and artificial intelligence related algorithms to process the data elements. In some embodiments, the one or more artificial intelligence models and/or trained learning models can include deep learning, machine learning, neural networks, computer vision and similar advanced artificial intelligence-based technologies.

In some embodiments, a second aspect of the anatomical features and/or representations can be processed via one or more specific artificial intelligence models at step 1220. In some embodiments, the second aspect of the anatomical features can be processed during step 1220 while the first aspect is being processed. It will be appreciated by one skilled in the art that the system and process described is not limited to only a first and second aspect of the anatomical features being evaluated, but instead can include the evaluation and processing of a plurality of aspects of the anatomical features. At step 1220, the process evaluates all data elements extracted and saved in the memory 730 to generate a non-rigid shape reference in step 1225 based on an evaluation of all accumulated data elements.

At step 1225, the system uses the artificial intelligence model(s) to create a non-rigid shape reference based on one or more feature extracted from the patient-specific 2D image file 725 package at step 1205, which is then used, in some embodiments, to transform contours and surface features of the 2D image patient image files 725 into a 3D digital representation of the patient anatomy, including one or more patient-specific surface(s). In some embodiments, the patient-specific surfaces can include one or more porous areas, smooth or textured surface features, features of different thicknesses, and/or other surface features. It will be appreciated that other patient-specific configurations and surfaces are contemplated.

At step 1230, a 3D device model of the anatomical feature is created based on the non-rigid shape reference generated. In some embodiments, the data elements are transformed at step 1230 from a 2D representation to a 3D digital representation and then the associated point cloud space is aligned with an artificial intelligence model trained based on or more aspects of patient data to generate a lower-dimensional representation model of the patient anatomy. At step 1235, a CAD file for at least one patient-specific implant is generated. As described above in connection with FIGS. 1-7, the patient-specific implant can also include a device, instrument, or other objects.

At step 1235, the process generates and/or retrieves the CAD model data 1260, described in connection with FIG. 11, to include in the generated CAD file. In some embodiments, the CAD file may be generated based on one or more of the 3D digital representations of the anatomical feature of a particular patient, the patient-specific image files 725, and the output of the one or more artificial intelligence training model, which can analyze the plurality of data elements included in the memory 730, or retrieved from other data sources, in some embodiments. In some embodiments, the system can incorporate one or more patient-specific surfaces in the CAD file, including but not limited to one or more porous areas comprising a lattice structure configured to promote osseointegration with one or more anatomical features, including tissue, bone, muscle, nerve, etc. It will be appreciated that the system can design and generate one or more surfaces and/or textures to the generated CAD file at step 1235 and/or to the implant/device generated at step 1240 including but not limited to a lattice structure, surface texture, holes or apertures, threads, etc.

Using the generated CAD file from step 1235, the system can then create or generate the personalized patient-specific implant at step 1240. In some embodiments, a plurality of implants may be generated at step 1240. For example, the system can create a test implant in addition to the implant to be used in the patient, for a provider to practice before the surgical procedure. In another non-limiting embodiment, the process 1200 may generate a plurality of implants in various sizes at step 1240. In this example, the provider can field-test the appropriate fit of the implant as needed during the operation without requiring any modifications to the implant. In some embodiments, the test implant can be compared to the 3D digital representation, either physically or digitally, to facilitate the field-test, as described in more detail in connection with FIG. 7. In some embodiments, the system can receive feedback data to be processed in the feedback model 1125 to improve the advanced analytic and artificial intelligence processes described herein.

FIG. 13 illustrates a training process 1300 for iteratively training one or more artificial intelligence models used in the implant generation process 700 (see FIG. 7). The training process 1300 can be configured to perform various advanced data analysis and modeling processes. In one example, the training process 1300 generates and iteratively trains training models, including but not limited to the particular training model 735 and the specific training model 750, for providing dynamic analysis of a plurality of data elements related to one or more aspects of anatomical features and designing a customized personalized implant based on an evaluation of all available data elements within a memory 730. For example, the process 1300 can be configured to generate, train, and execute a plurality of nodes, neural networks, gradient boosting algorithms, mutual information classifiers, random forest classifications, and other artificial intelligence-related algorithms.

At step 1305, the system receives (or retrieves from the memory 730) an image file package including patient population data 715, anatomy data 720, a series of 2D images associated with a particular anatomical feature, and other patient data (e.g., medical history). In some embodiments, the step 1305 described above can apply to training the particular artificial intelligence model 735. In some embodiments, the system is designed to process patient population data 715 including information from thousands of patients (e.g., medical history, injuries, surgeries, diseases, disorders, allergies, height, weight, etc.). The patient population data 715 can be received by a user interface 710 and/or retrieved from memory 730.

In some embodiments, the step 1305 may instead include receiving implant population data 755 for training the specific artificial intelligence model 750. In some embodiments, the step 1305 can include receiving both patient population data 715 and implant population data 755 for training an ensemble artificial intelligence model comprising both the particular artificial intelligence model 735 and the specific artificial intelligence model 750. In one non-limiting embodiment, the system can identify that the patient needs ankle surgery and retrieve anatomy data 720 related to the ankle from the patient population data 715 in order to train the artificial intelligence model. The system can train the implant/device model 750 based on a specific type of implant (e.g., tibial), implants for a single anatomical feature (e.g., ankle or foot), or for all implants and fine-tuned or with updated emphasis guidelines based on the particular procedure to be performed.

At step 1310, the system can extract aspects from the image file package received at step 1305, which includes known parameters used to iteratively train the one or more artificial intelligence training models. The system in step 1310, can extract and process a plurality of input data sets associated with a specific data element type, wherein each of the plurality of input data sets can have multiple data types. In one embodiment, a specific anatomical feature of the process 1200 may include multiple associated input data sets.

At step 1315, the system can input the data elements corresponding to the extracted aspects as a training input data set into one or more artificial intelligence training models. In one non-limiting example, the system can iteratively train the artificial intelligence training models based on multiple training input data sets of different data types, including data elements associated with a particular anatomical feature, particular implant, parameter, characteristic, or other aspects.

The system, in step 1320, receives a plurality of parameter values as outputs from the plurality of trained learning models. In some embodiments, the system can use the plurality of output parameter values to generate the non-rigid shape references and/or the 3D digital representation of the anatomical feature. In at least this way, the system can utilize a plurality of trained learning models to output specific parameters or metrics tailored to certain design details of the anatomical feature. In one example, if an anatomical feature has anatomy data 720 associated with a specific deformity, the system can use a artificial intelligence training model based primarily on data analysis of patient population data 715 and anatomy data 720 related to the deformity, or other parameters that may influence the deformity. Alternatively, the system could also utilize a combination of multiple training models where the deformity is one of a plurality of parameters, in addition to the surface, texture, etc., wherein the process 1300 can recognize and provide a personalized implant designed for the specific patient based on data elements from all available patient records associated with patient population data 715, anatomy data 720, image data 1150, implant data 1155, CAD model data 1160, and other data. It will be appreciated by one skilled in the art that a combination of multiple parameters can be used in a single training loop to provide a personalized implant based on a high level of certainty.

In some embodiments, the artificial intelligence model 735 is a particular artificial intelligence model wherein the system includes training the model to create a non-rigid shape reference to transform 2D anatomical features into 3D data representations of the anatomy in order to generate a 3D digital representation 740 for the patient-specific anatomy. For example, in one embodiment, the system may extract initial data and features from image files associated with many thousands of patients as it relates to a particular type of anatomical feature and/or procedure and/or implant. In one embodiment, the system may extract initial data and features from the patient-specific image files 725 to construct a data representation of patient anatomy (e.g., a diseased ankle of a particular patient).

Additionally, at step 1320, the system can generate a 3D device model from the output of the one or more artificial intelligence training models. In some embodiments, when training the particular artificial intelligence model 735, the 3D device model may be a 3D digital representation 740 generated based on a non-rigid shape reference created as an output of the one or more artificial intelligence training models. In some embodiments, the 3D model may be a 3D device model 765 to compare to the anatomy model 740, for example when training the specific artificial intelligence model 750. In some embodiments, the system can train a specific artificial intelligence model 750 using implant population data 755 including implant information and data related to a plurality of implants designed for a plurality of patients. In some embodiments, the system can train the specific artificial intelligence model 750 based on implant population data 755 for a single anatomical feature or for a plurality of anatomical features with fine-tuned emphasis guidelines for specific anatomical features to provide a trained specific artificial intelligence model 750 designed to generate a CAD file 760 and/or 3D device model 765 for a customized implant 770.

In some embodiments, the system can compare the 3D digital representation 740 to a known 3D digital representation and the training process can include updating one or more emphasis guidelines 1330 of the artificial intelligence training model in order to update the model based on patient-specific surfaces. In some embodiments, system can update one or more aspects of the 3D digital representation, rerunning the artificial intelligence training model to determine if the output of the comparing step 1325 the generated 3D digital representation to the known 3D digital representation is within a preconfigured threshold 1335. If the output of the comparing step 1325 is within the preconfigured threshold as determined by step 1335, the updated emphasis guidelines may be saved 1340, and the system can save the updated artificial intelligence training model as the trained artificial intelligence model.

At step 1325, the generated 3D digital representation can then be compared to the known parameters for the training input data set. At step 1330 if the output of compare step of 1325 is not within a preconfigured threshold of the known parameters, one or more emphasis guidelines can be updated for a plurality of nodes within the artificial intelligence training model. In some embodiments, for example while training the particular artificial intelligence model 735, the comparison step 1325 can include comparing the generated 3D digital representation to a known 3D digital representation in the patient population data 715. In some embodiments, for example while training the specific artificial intelligence model 750, the comparison step 1325 can include comparing the generated 3D device model/file to a known 3D device model/file in the implant/device population data 755.

In some embodiments, the comparison step 1325 can be performed by one or more artificial intelligence models, including but not limited to the particular artificial intelligence model 735 and/or a specific artificial intelligence model 750. In various embodiments, one or more artificial intelligence models, including but not limited to the particular artificial intelligence model and/or the specific artificial intelligence model, can be trained based on a specific anatomical feature, surface topography, lattice structure, or aspects thereof. It will be appreciated by one skilled in the art that various artificial intelligence models can include models trained for a specific patient, anatomical feature, surgery, or disease state, based on one or more patient-specific files and/or implant parameters. In some embodiments, the artificial intelligence model compares an output to a known 3D digital representation stored in memory 730 and or from the patient population data 715 to iteratively train the artificial intelligence model and adjust emphasis guidelines. In some embodiments, the one or more artificial intelligence model(s) is provided in the form of an ensemble artificial intelligence model comprising the particular artificial intelligence model 735 and the specific artificial intelligence model 750. It will be understood by one skilled in the art that the combination and configuration of the one or more artificial intelligence model(s) is not limited to those described in connection with FIG. 13 but can include other configurations of one or more advanced artificial intelligence models.

The system may then, in some embodiments, adjust, change, or add data to the 3D digital representation 740 based on other patient population data 715 (e.g., anatomy aspects and feature from patients with similar data elements including similar images, similar size, similar injuries, etc.). The system can further adjust a 3D digital representation 740 based on one or more patient-specific data elements (e.g., provider notes, other images, etc.). In some embodiments, the system can fine-tune or otherwise adjust the generated 3D digital representation 740 by adjusting the emphasis guidelines for the training model, or by directly editing features of the generated 3D digital representation 740 without adjusting the training model 735.

As used throughout the present disclosure, "emphasis guidelines" can include weights, ranks, or other metrics associated with iteratively training an artificial intelligence or machine learning training model to improve the accuracy and relevance of generated results.

The system can update the one or more emphasis guidelines based on the results of the step 1325, to iteratively train and improve the training model in step 1330. The one or more emphasis guidelines of the system can be updated for a plurality of nodes within the raw training models based on the results of the comparing step, to iteratively train and improve the training models. When the emphasis guidelines are updated at step 1330, the artificial intelligence training model can be rerun, re-executed, or the data otherwise processed again through the algorithm(s) to determine if the generated 3D digital representation 740 is within a predefined threshold of the known 3D digital representation, based on the output of the comparing step 1325.

In some embodiments, the predefined threshold can include various tolerance levels, which can be adjusted based on specific parameters. In one non-limiting example, a size of an anatomical feature relative to another anatomical feature may have a smaller threshold tolerance level than surface structure deviations. In further embodiments, the predefined threshold can be modified dependent on the particular implant to be generated, on specific characteristics of the anatomical feature being modeled, or on any number of other factors.

In some embodiments, the system can further use the artificial intelligence training model that has been updated with the saved emphasis guidelines to further process input data as the iteratively trained artificial intelligence training model. In some embodiments, the iteratively trained artificial intelligence training model can include the particular artificial intelligence model 735 and/or the specific artificial intelligence model 750 and/or the ensemble artificial intelligence model comprising both the particular 735 and specific 750 artificial intelligence models. The trained artificial intelligence model(s) can continue to be updated as additional patient population data 715 is received and processed by the system.

At step 1335, when the generated 3D digital representation output of the artificial intelligence training model is within a preconfigured threshold of known parameters for the training input data sets, as determined by the comparing step of 1325, the system can save the plurality of artificial intelligence training models as trained artificial intelligence models and save the one or more updated emphasis guidelines from step 1330 in the memory 730 in step 1340.

Also, the system can include one or more secondary metrics as parameters in one or more processes to iteratively train a training model or a plurality of artificial intelligence training models. When used throughout the present disclosure, one skilled in the art will understand that processes for "iteratively training the artificial intelligence training model" can include machine learning processes and other advanced artificial intelligence processes. For example, the system and processes of the present disclosure can perform diagnostics, and image analysis, generate tasks or action items, provide customized recommendations according to user settings and preferences, generate 3D device models, CAD files, and personalized implant designs, generate notifications, and similar processes. In some embodiments, the system may use additional inputs and/or feedback loops to an iterative training process for a personalized implant generation process based on a plurality of parameters and adjustable metric values.

In some embodiments, the system can include a process for iteratively training an artificial intelligence model (or multiple artificial intelligence models) according to some embodiments of the present disclosure. In various embodiments, the iteratively trained artificial intelligence model(s) can be designed to perform various advanced data analysis and modeling processes. In one example, the system generates and iteratively trains the artificial intelligence training model to provide dynamic data analysis, and the advanced analytics can be used to generate a 3D device model, and CAD file, and print an implant/device. In some embodiments, these processes can be performed by multiple artificial intelligence models, or multiple aspects of a single artificial intelligence model (e.g., an ensemble model), or a combination thereof. In one non-limiting embodiment, the artificial intelligence training model(s) can be designed to generate, train, and execute a plurality of nodes, neural networks, gradient boosting algorithms, mutual information classifiers, random forest classifications, and other machine learning and artificial intelligence-related algorithms.

It will be appreciated by one skilled in the art that the system and processes described herein can include different and/or additional details, data elements, measurements, parameters, metrics, and implants than those described in the specific embodiments herein.

Additionally, the embodiments described herein are further directed to an improved system and methodology for using artificial intelligence to analyze and process patient data from a dynamic database to generate a personalized surgical implant/device 770. These embodiments represent an advancement over the prior art for several reasons, including that the systems and methods are capable of complex and efficient data analysis related to a plurality of different anatomical feature aspects and parameters. While the prior art may utilize a best fit or nearest neighbor to develop surgical implants, the embodiments described herein do not limit data analysis to the best fit or nearest neighbor techniques and instead intelligently considers all relevant data elements associated with an anatomical feature, including those not directly related. In a non-limiting example, the system and processes described herein can evaluate anatomy data 720 related to a joint other than the one being replaced in surgery, because the system recognizes that injuries to a different joint may impact the particular joint being replaced, for which the implant is being generated. The embodiments can include measuring the changes to anatomical features over time, accumulating these measurements across a memory 730 of population patient data 715 and/or patient-specific data received or extracted, performing statistical analysis on the accumulated measurements, performing advanced diagnostics, and producing one or more customized outputs.

According to particular embodiments, the system may automatically link or associate data included in the 3D digital representation 740 to one or more parameters according to the advanced analytic processes described herein. In some embodiments, the linked data can include information related to joint replacement, including anatomical features of common joints. Non-limiting examples can include foot, ankle, shoulder, elbow, hips, knees, tracheal stents, etc. It will be understood by those skilled in the art that the embodiments described herein are not limited to a joint replacement but can be applied to the generation of other implants, medical devices, instruments, or other objects. In some embodiments, the implant generation process 700 can evaluate the anatomy data 720 in light of the patient population data 715, the patient's image files 725, and a patient's personal information or file history to further personalize the generated implant 770.

While the particular embodiments described herein relate to healthcare-based applications. It will be recognized and appreciated that the systems and processes described herein are also applicable to at least, but not including, other types of design services. For example, the systems and methods described herein could be used to analyze and generate custom solutions related to architecture, construction, engineering, repairs, art restoration, hobby electronics, advanced computing, etc.

It will be appreciated by one skilled in the art that this embodiment is only a non-limiting example used to illustrate that the system and processes are designed to dynamically provide an advanced artificial intelligence model for evaluating a plurality of data elements associated with an anatomical feature, including data elements directly related to other anatomical features but that may have an impact on the anatomical feature being evaluated. Additionally, the non-limiting example can be used for personalized implant generation requests and advanced data processing techniques across a plurality of systems and applications and can apply to a plurality of different services and industries.

Computer program code that implements the functionality described herein typically comprises one or more program modules that may be stored on a data storage device. This program code, as is known to those skilled in the art, usually includes an operating system, one or more application programs, other program modules, and program data. A user may enter commands and information into to the computer through a keyboard, touch screen, pointing device, a script containing computer program code written in a scripting language, or other input devices, such as a microphone, etc. These and other input devices are often connected to the processing unit through known electrical, optical, or wireless connections.

The computer that affects many aspects of the described processes will typically operate in a networked environment using logical connections to one or more remote computers or data sources, which are described further below. Remote computers may be another personal computer, a server, a router, a network PC, or other common network nodes common network node, and typically include many or all of the elements described above relative to the main computer system in which the systems are embodied. The logical connections between computers include a LAN, a WAN, virtual networks (WAN or LAN), and wireless LAN ("WLAN") that are presented here by way of example and not limitation. Such networking environments are commonplace in office-wide or enterprise-wide computer networks, intranets, and the Internet.

When used in a LAN or WLAN networking environment, a computer system implementing aspects of the system is connected to the local network 1170 through a network interface or adapter. When used in a WAN or WLAN networking environment, the computer may include a modem, a wireless link, or other mechanisms for establishing communications over the WAN, such as the Internet. In a networked environment, program modules depicted relative to the computer, or portions thereof may be stored in a remote data storage device. It will be appreciated that the network connections described or shown are non-limiting examples and other mechanisms of establishing communications over WAN or the Internet may be used.

Additional aspects, features, and processes of the claimed systems will be readily discernible from the description herein, by those of ordinary skill in the art. Many embodiments and adaptations of the disclosure and claimed systems other than those herein described, as well as many variations, modifications, and equivalent arrangements and processes, will be apparent from or reasonably suggested by the disclosure and the description thereof, without departing from the substance or scope of the claims. Furthermore, any sequence(s) and/or temporal order of steps of various processes described and claimed herein are those considered to be the best mode contemplated for carrying out the claimed systems. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed systems. In addition, some steps may be carried out simultaneously, contemporaneously, or in synchronization with other steps.

Aspects, features, and benefits of the claimed devices and processes for using the same will become apparent from the information disclosed in the exhibits and the other applications as incorporated by reference. Variations and modifications to the disclosed systems and processes may be affected without departing from the spirit and scope of the novel concepts of the disclosure.

It will, nevertheless, be understood that no limitation of the scope of the disclosure is intended by the information disclosed in the exhibits or the applications incorporated by reference; any alterations and further modifications of the described or illustrated embodiments, and any further applications of the principles of the disclosure as illustrated therein are contemplated as would normally occur to one skilled in the art to which the disclosure relates. The description of the disclosed embodiments has been for illustration and description and is not intended to be exhaustive or to limit the devices and processes for using the same to the precise forms disclosed. Many modifications and variations are possible in light of the above teaching.

The embodiments were chosen and described to explain the principles of the devices and processes for using the same and their practical application to enable others skilled in the art to utilize the devices and processes for using the same and various embodiments and with various modifications as are suited to the particular use contemplated. Alternative embodiments will become apparent to those skilled in the art to which the present devices and processes for using the same pertain without departing from their spirit and scope. Accordingly, the scope of the present devices and processes for using the same is defined by the appended claims rather than the description and the embodiments described therein.

What is claimed is:

1. A medical device production process comprising:
   populating a database with:
      a plurality of 2D image packages, each of the plurality of 2D image packages comprising a series of 2D image files of patient-specific anatomy;
      a plurality of patient anatomical representations, each of the plurality of patient anatomical representations associated with at least one of the plurality of 2D image packages;
      a plurality of patient-specific device files, each of the plurality of patient-specific device files associated with at least one of the plurality of patient anatomical representations;
   receiving a particular 2D image package associated with a particular patient and including a series of 2D images files associated with an anatomical feature of the particular patient;
   extracting one or more aspects of the anatomical feature of the particular patient from the particular 2D image package;
   processing the one or more aspects of the anatomical feature via an artificial intelligence model to create a non-rigid shape reference based upon the plurality of patient anatomical representations and patient-specific device files; and
   generating a digital representation of at least one patient-specific device based on the non-rigid shape reference of the anatomical feature of the particular patient and the database.

2. The process of claim 1, wherein the patient-specific device comprises a patient-specific implant.

3. The process of claim 1, wherein the patient-specific device comprises a patient-specific instrument.

4. The process of claim 1, wherein:
   the artificial intelligence model is a particular artificial intelligence model; and
   generating the digital representation of the at least one patient-specific device is based on:
      the 3D digital representation of the anatomical feature of the particular patient;
      the plurality of patient-specific device files; and
      processing the one or more aspects of the anatomical feature via a specific artificial intelligence model.

5. The process of claim 4, wherein the specific artificial intelligence model outputs a patient-specific device file based on a compilation of the plurality of patient-specific device files.

6. The process of claim 5, wherein generating the digital representation of the at least one patient-specific device comprises processing the one or more aspects of the anatomical feature, the 3D digital representation of the anatomical feature of the particular patient, and the plurality of patient-specific device files via the artificial intelligence model.

7. The process of claim 4, wherein the specific artificial intelligence model is the particular artificial intelligence model.

\* \* \* \* \*